US005821084A

United States Patent [19]
Olmsted et al.

[11] Patent Number: 5,821,084
[45] Date of Patent: Oct. 13, 1998

[54] OSTEOBLAST-TESTICULAR PROTEIN TYROSINE PHOSPHATASE

[75] Inventors: Elizabeth Ann Olmsted, Devon, Pa.; Laura Jeanne Mauro, Ann Arbor, Mich.; Alan Robert Davis, Wayne, Pa.; Jack Edward Dixon, Ann Arbor, Mich.

[73] Assignees: The Regents of the University of Michigan, Ann Arbor, Mich.; American Home Products Corporation, Madison, N.J.

[21] Appl. No.: 342,930

[22] Filed: Nov. 21, 1994

[51] Int. Cl.⁶ .................................................... C12N 15/52
[52] U.S. Cl. .................. 435/69.1; 435/320.1; 435/252.3; 435/325; 536/23.5; 536/24.3
[58] Field of Search .................................. 536/23.2, 24.3; 435/69.1, 320.1, 252.3, 240.2, 325; 935/23, 55, 70, 72

[56] References Cited

U.S. PATENT DOCUMENTS

5,294,538  3/1994  Beach ........................................ 435/21

FOREIGN PATENT DOCUMENTS

WO 92/01050  1/1994  WIPO .
WO 95/07935  3/1995  WIPO .

OTHER PUBLICATIONS

Aronow et al., "Factors that promote progressive development of the osteoblast phenotype in cultured fetal rat calvaria cells" *J. Cell. Physiol.* (1990) 143:213–221.
Brady–Kalnay et al., "Homophilic binding of PTPμ, a receptor–type protein tyrosine phosphatase, can mediate cell–cell aggregation" *J. Cell. Biol.* (1993) 122:961–972.
Charbonneau et al., "Human placenta protein–tyrosine–phosphatase: Amino acid sequence and relationship to a family of receptor–like proteins" *Proc. Natl. Acad. Sci. USA* (1989) 86:5252–5256.
Charbonneau et al., "1002 protein phosphatases?" *Ann. Rev. Cell Biol.* (1992) 8:463–493.
Charbonneau et al., "the leukocyte common antigen (CD45): A putative receptor–linked protein tyrosine phosphatase" *Proc. Natl. Acad. Sci. USA* (1988) 85:7182–7186.
Clohisy et al., "Parathyroid hormone induces c–fos and c–jun messenger RNA in rat osteoblastic cells" *Mol. Endocrinol.* (1992) 6:1834–1842.
Endo et al., "Identification and cloning of a novel receptor–like protein tyrosine phosphatase from human osteoblasts" *American Society of Bone and Mineral Research Meeting* (1993) 8:S5. (abstract No. 32).
Frohman et al., "Rapid production of full–length cDNAs from rare transcripts: Amplification using a single gene–specific oligonucleotide primer" *Proc. Natl. Acad. Sci. USA* (1988) 85:8998–9002.
Genovese et al., "Construction of DNA swquences complementary to rat $\alpha_1$ and $\alpha_2$ collagen mRNA and their use in studying the regulation of type I collagen synthesis by 1,25–dihydroxyvitamin D" *Biochem.* (1984) 23:6210–6216.

Grimes et al., "A rat histone H4 gene closely associated with the testis–specific H1t gene" *Exp. Cell Res.* (1987) 173:534–545.
Guan et al., "Evidence for protein–tyrosine–phosphatase catalysis proceeding via a cysteine–phospate intermediate" *J. Biol. Chem.* (1991) 26:17026–17030.
Guan et al., "Cloning and expression of a protein–tyroisne–phosphatase" *Proc. Natl. Acad. Sci. USA* (1990) 87:1501–1505.
Hunter, "All tail of two *src's*: Mutatis mutandis" *Cell* (1987) 49:1–4.
Hunter et al., "Protein–tyrosine kinases" *Ann. Rev. Biochem.* (1985) 54:897–930.
Kerszenbaum, "Mammalian spermatogenesis in vivo and in virto: A partnership of spermatogenic and somatic cell lineages" *endocrine Rev.* (1994) 15:116–134.
Kohno et al., "Isolation and characterization of a cDNA clone for the amino–terminal portion of the pro–$\alpha$ 1 (II) chain of cartilage collagen" *J. Biol. Chem.* (1984) 259:13668–13673.
Kreuger et al., "Structural diversity and evolution of human receptor–like protein tyrosine phosphatases" *EMBO J.* (1990) 9:3241–3252.
Lian et al., "Structure of the rat osteocalcin gene and regulation of vitamin D–dependent expression" *Biochem.* (1988) 86:1143–1147.
Matthews et al., "Characterization of hematopoietic intracellular protein tyrosine phosphatases. Description of a phosphatases containing an SH2 domain and another enriched in proline, glutamic acid, serine, and threonine–rich sequences" *Mol. Cell. Biol.* (1992) 12:2396–2405.
Maurel et al., "Phosphacan, a chondroitin sulfate proteoglycan of brain that interacts with neurons and neural call–adhesion molecules, in an extracellular variant of a receptor––type protein tyrosine phosphatase" *Proc. Natl. Acad. Sci. USA* (1994) 91:2512–2516.
Mauro et al., "Isolation of a regulated protein tyrosine phosphatase specific to bone and testis" *ASBMB Satellite Meeting* (1994) (Abstract).

(List continued on next page.)

*Primary Examiner*—John Ulm
*Assistant Examiner*—Karen E. Brown
*Attorney, Agent, or Firm*—Morrison & Foerster LLP

[57] ABSTRACT

A previously undiscovered transmembrane protein tyrosine phosphatase expressed only in bone and testis, osteotesticular protein tyrosine phosphatase (OST-PTP), has been identified, cloned, sequenced, expressed and subjected to enzymatic analysis. Also, a truncated osteoblast specific form (OST) containing the OST-PTP receptor but lacking the catalytic domain was identified and characterized. Based on the unique expression pattern of OST-PTP and OST during osteogenesis, assays can be used to screen for abnormal bone growth patterns and metabolic bone diseases. Moreover, this novel protein provides a specific target for use in conventional and gene therapies directed at treatment of osteoporosis, osteopetrosis and other bone metabolic disorders.

30 Claims, 5 Drawing Sheets

OTHER PUBLICATIONS

Mauro et al., "Identification of novel protein tyrosine phosphatases in bone" *Endocrine Society Meeting* (Jan. 24, 1993) (Abstract).

Morala et al., "Reversible tyrosine phosphorylation of cdc2: Dephosphorylation accompanies activation during entry into mitosis" *Cell* (1989) 58:193–203.

Noda et al., "cDNA cloning of alkaline phosphatase from rat osteosarcoma (ROS 17/2.8) cells" *J. Bone & Mineral Res.* (1987) 2:161–164.

Ohashi et al., "Ligand–induced activation of chimeric receptors between the erythropoietin receptor and receptor tyrosine kinases" *Proc. Natl. Acad. Sci. USA* (1994) 91:158–162.

Oldberg et al., "Cloning and sequence analysis of rat bone sialoprotein (osteopontin) cDNA reveals an Arg–Gly–Asp cell–binding sequence" *Proc. Natl. Acad. Sci. USA* (1986) 83:8819–8823.

Pingel, "Evidence that the leukocyte–common antigen is required for antigen–induced T lymphocyte proliferation" *Cell* (1989) 58:1055–1065.

Ralph et al., "Structural variants of huaman T200 glycoprotein (leukocyte–common antigen)" *EMBO J.* (1987) 6:1251–1257.

Remington's Pharmaceutical Sciences, 16th ed., (1980) Mack Publishing Co., Easton, Pennsylvania.

Riedel et al., "A chimaeric receptor allows insulin to stimulate tyrosine kinase activity of epidermal growth factor receptor" *Nature* (1986) 324:68–70.

Sakamaki et al., "Ligand–dependent activation of chimeric receptors with the cytoplasmic domain of the interleukin–3 receptor βsubunit ($\beta_{IL3}$)" *J. Biol. Chem.* (1993) 268:15833–15839.

Sambrook et al., *Molecular Cloning: A Laboratory Manual*, 2nd ed., (1989) Cold Spring Harbor Laboratory Press, Cold Spring Harbor, New York.

Schmidt et al., "Identification of an osteoclast specific protein tyrosine phosphatase and its potential role in osteoclast fusion and bone resorption" *American Society of Bone and Mineral Research Meeting* (1993) 8:S144. (abstract no. 111).

Scott et al., "Parathyroid hormone induces transcription of collagenase in rat osteoblastic cells by a mechanism using cyclic adenosine 3',5'–monophosphate and requiring protein synthesis" *Mol. Endocrinol.* (1992) 6:2153–2159.

Shen et al., "A protein–tyrosine phosphatase with sequence similarity to the SH2 domain of the protein–tyrosine kinases" *Nature* (1991) 352:736–739.

Skinner, "Cell–cell interactions in the testis" *Endocrine Rev.* (1991) 12:45–77.

Soriano et al., "Targeted disruption of the c–src proton–oncogene leads to osteopetrosis in mice" *Cell* (1991) 64:693–702.

Streuli et al., "A new member of the immunoglobulin superfamily that has a cytoplasmic region homologous to the leukocyte common antigen" *J. Exp. Med.* (1988) 168:1553–1562.

Tonks et al., "Demonstration that the leukocyte common antigen CD45 is a protein tyrosine phospatase" *Biochem.* (1988) 27:8695–8701.

Trail et al., "Cure of xenografted human carcinomas by BR96–doxorubicin immunoconjugates" *Science* (1993) 261:212–215.

Ullrich et al., "Signal transduction by receptors with tyrosine kinase activity" *Cell* (1990) 61:203–212.

Walton et al., "Protein tyrosine phosphatases" *Ann. Rev. Biochem.* (1993) 62:101–120.

OSTEOBLAST-TESTICULAR PROTEIN TYROSINE PHOSPHATASE

FIELD OF THE INVENTION

The present invention in the field of biochemistry and cell and molecular biology relates to the discovery of a novel transmembrane receptor-type protein tyrosine phosphatase termed osteotesticular protein tyrosine phosphatase (OST-PTP). The cloning and sequencing of the RNA transcript encoded by the OST-PTP gene is described as weel as the expression and enzymatic characterization of the OST-PTP protein. The invention further relates to methods for screening compounds capable of binding to and inhibiting or stimulating OST-PTP activity and use of this invention to diagnose and treat bone metabolic disorders via targeted conventional treatment or gene therapy.

BACKGROUND OF THE INVENTION

Protein tyrosine phosphorylation is important in the regulation of cell growth, proliferation and differentiation as well as in the homeostasis of metabolic processes. A functional relationship between tyrosine phosphorylation and cell processes has been demonstrated by studies on the activity of enzymes such as phospholipase C (PLC) (Hunter et al., 1985, *Ann. Rev. Biochem.* 54:897–930, Ullrich et al., 1990, *Cell* 61:203–212). Growth factor stimulation of certain cells in culture increases the level of tyrosine phosphorylation as well as the activity of PLC. The protein tyrosine kinases are responsible for this phosphorylation of tyrosine residues within cellular proteins. It is important to recognize that the degree and pattern of phosphorylation by these protein tyrosine kinases can be regulated by an opposing dephosphorylation catalyzed by a family of enzymes, the protein tyrosine phosphatases (PTP). In this way, protein tyrosine phosphatases help calibrate the level of tyrosine phosphorylation in a cell and provide another regulatory control system to govern cellular processes.

The protein tyrosine phosphatases are a structurally diverse family of proteins which include transmembrane molecules known as receptor-like PTPs and non-transmembrane molecules known as intracellular PTPS. These proteins all posses a conserved catalytic domain containing the active site sequence, (I/V) HCXAGXXR (S/T)G (SEQ ID NO:3). The cysteine residue within this active site is critical for catalytic activity, forming a phosphocysteine intermediate during the phosphate monoester hydrolysis. Typically, the intracellular PTPs possess a single catalytic domain, whereas the receptor-like PTP often have two cytoplasmic catalytic domains separated by 56–57 amino acids. Fourteen of the sixteen transmembrane receptor-like PTP proteins previously isolated contain two such domains (Walton et al., 1993, *Ann. Rev. Biochem.* 62:101–120).

One of the best characterized receptor-like tyrosine phosphatases described is CD45 or leukocyte common antigens (Ralph et al., 1987, *EMBO J.* 6:1251–1257, Charbonneau et al., 1989, *Proc. Natl. Acad. Sci. USA,* 85:7182–7186), which consists of a single polypeptide comprised of an extracellular domain, a membrane spanning domain and two nearly identical intracellular catalytic domains of approximately 300 amino acids each. CD45 comprises a group of membrane glycoproteins expressed exclusively in hemopoietic (except late erythroid) cells, derived from a common gene by alternative splicing events involving the amino terminus of the proteins. Other receptor-like PTP molecules contain one to three tandem Ig-like domains near their N-termini in the extracellular domain often adjacent to multiple fibronectin type III-like repeats (FN-III) resembling the N-CAM family of neural cell adhesion molecules. Recent evidence indicates that PTP molecules with the FN-III motif not only have ligand binding properties but are involved in cell adhesion e.g. receptor-like PTP-$\mu$ is involved in homophilic binding mediated cell-cell aggregation (Brady-Kalnay et al., 1993, *J. Cell. Biol.* 122:961–972) .

Accumulating evidence indicates that the process of dephosphorylation of tyrosine can serve as an important regulatory mechanism in cellular function. For example, dephosphorylation of a C-terminal tyrosine residue stimulates tyrosine kinase activity in the src family of tyrosine kinases (Hunter, T., 1987, *Cell* 49:1–4). Also, tyrosine dephosphorylation appears to be an obligatory step in the mitotic activation of the maturation promoting factor (MPF) kinase (Morla et al., 1989, *Cell* 58:193–203) . However only minimal information regarding the cellular function of particular PTP molecules is presently available. Small, soluble PTP enzymes may have a "housekeeping" function (Tonks et al., 1988, *Biochem.* 27: 8695–8701). On the other hand, the receptor-like PTP molecules appear to be more specific both in their expression and activity by virtue of their location in the cell membrane and potential regulation by extracellular ligands.

A definitive role for CD45 has been established in T cells where CD45 activated a lymphocyte specific kinase (p56$^{lck}$) by dephosphorylation of tyrosine residue 505 leading to T cell activation. CD45 deficient T cell clones failed to proliferate upon receptor stimulation with a specific antigen (Pingel, J. T., 1989, *Cell* 58:1055–1065). Indirect evidence indicates that a protein tyrosine phosphatase cdc25 was involved in control of the timing of mitosis by regulation of a protein serine/threonine kinase, the cdc2 gene product of p34 cdc2. A mutant form of p34 cdc2, in which tyrosine 15 was changed to phenylalanine, rescued a cdc25 temperature sensitive mutant at the restrictive temperature. Therefore, dephosphorylation of cdc2 by the tyrosine phosphatase cdc25 is necessary for initiation of cell division.

Recent studies have extended the role of protein tyrosine phosphorylation to bone metabolism. Targeted disruption of the mouse c-src proto-oncogene, a protein tyrosine kinase, caused osteopetrosis, a disease characterized by absence of appropriate bone resorption due to impaired osteoclast function (Soriano et al., 1991, *Cell* 64:693–702). There were no abnormalities detected in brain or platelets despite the fact that these were known to be the sites of highest c-src expression. Congenital ostepetrosis, as exhibited by the op/op mouse, is also due to a disruption of tyrosine phosphorylation. These animals lack biologically active macrophage colony stimulating factor (M-CSF), which serves as the ligand for c-fms, a proto-oncogene encoding a tyrosine kinase which is necessary for osteoclast function. These limited data regarding the dramatic effect of inhibition of protein tyrosine phosphorylation in bone metabolism point out the need in the art to increase our understanding of protein tyrosine phosphatase function in this tissue, particularly since the biological role of PTP is to reduce the cellular level of protein tyrosine phosphorylation.

Two recent abstracts have reported the presence of protein tyrosine phosphatases in bone. In the first, a receptor-like PTP was identified in bone and brain but with maximal expression in growing cells and negligible expression in confluent cultures (Endo et al., 1993, "Identification and Cloning of a Novel Receptor-like Protein Tyrosine Phosphatase from Human Osteoblasts," *American Society of*

*Bone and Mineral Research Meeting* 8:S5). In a second abstract (Schmidt et al., 1993, "Identification of an Osteoclast Specific Protein Tyrosine Phosphatase and its Potential Role in osteoclast Fusion and Bone Resorption," *American Society of Bone and Mineral Research Meeting* 8:S144) mouse calvarial cells (osteoblasts) were incubated with bone marrow cells and 1,25 dihydroxyvitamin D3. Multinucleated cells that were tartrate-resistant acid phosphatase (TRAP) positive were enriched. They isolated the previously identified PTP-$\epsilon$ (Kreuger et al., 1990, *EMBO J.* 9:3241–3252) as a major PTPase transcript in these cells but reported that it was specific for the osteoclast. The timing of expression and spatial distribution of these protein tyrosine phosphatases as well as their transcript and protein molecular size indicate that they are clearly distinct from the present invention.

The identification of a tissue specific protein tyrosine phosphatase is important not only in understanding cellular functions but also as a basis for targeting therapeutic agents at a specific tissue without the risk of side effects in other cell types. Specific cell targeting has been demonstrated in the treatment of carcinomas. An immunoconjugate of the monoclonal antibody (BR96) and an anticancer agent, doxorubicin, bound to a tumor-associated antigen abundantly expressed on human carcinoma lines (Trail et al., 1993, *Science* 261:212–215). The BR96-doxorubicin immunoconjugate induced complete regression of xenografted human lung, breast and colon carcinomas growing subcutaneously in athymic mice. Similar principles have recently been applied to induce protein tyrosine phosphorylation and subsequent cell proliferation through the use of chimeric molecules. For example, chimeric molecules which linked the extracellular receptor domain of epidermal growth factor (EGF) to the cytoplasmic domain of the erythropoietin receptor successfully transmitted EGF proliferation signals (ohahi et al., 1994, *Proc. Natl. Acad. Sci. USA* 91:158–162). In another demonstration of this principle, various human cytokine receptors (interleukin-2, interleukin-4) as well as the murine erythropoietin receptor were separately linked to the cytoplasmic domain of the interleukin-3 receptor $\beta$ subunit $\beta$-Il3 (Sakamaki et al., 1993, *J. Biol. Chem.* 21:15833–15839). These chimeric receptors were functional in cells in that stimulation by the cytokine matching the receptor domain induced tyrosine phosphorylation and proliferation in the target cells.

Use of antibodies to target drug molecules has also been described previously. Trail described the cure of xenografted human carcinomas by an immunoconjugate of the monoclonal antibody BR96 with doxorubicin (*Science* 261:212–215 (1993)). BR96 binds to a tumor-associated antigen that is closely related to Lewis Y and is abundantly expressed on human carcinoma lines. Since BR96 binds the majority of human carcinomas of the breast, lung, and colon, it specifically targets the anticancer agent doxorubicin to these carcinomas. BR96-doxorubicin induced complete regressions and cures of xenografted human lung, breast, and colon carcinomas growing subcutaneously in athymic mice and cured 70 percent of mice bearing extensive metastases of a human lung carcinoma.

A similar targeting approach using immunoconjugates or chimeric molecules may be applicable to the important regulatory process of phosphatase induced tyrosine dephosphorylation with the identification of protein tyrosine phosphatase molecules bearing extracellular receptor domains which confer tissue specificity. The invention described herein is a protein tyrosine phosphatase with said requirements, i.e., a novel tissue specific PTP (as well as a truncated receptor transcript) which plays a critical role in the processes of osteogenesis and bone remodeling and shows stage-specific expression in the seminiferous tubules during the process of spermatogenesis.

DETAILED DESCRIPTION OF THE INVENTION

The present invention includes a unique mammalian (rat) receptor-like tyrosine phosphatase protein expressed specifically in bone and testis and termed osteotesticular protein tyrosine phosphatase (OST-PTP). The naturally occurring protein is normally expressed exclusively in bone predominantly during osteoblast proliferation and differentiation; and in the basal seminiferous tubules of the testis concomitant with spermatid maturation during stages I–VII and XII–XIV. The substantially pure OST-PTP protein may be produced by biochemical purification of the naturally occurring protein. Alternatively, the OST-PTP protein may not be of natural origin, such as one prepared by utilizing chemical synthesis technology or produced by recombinant means in prokaryotic or eukaryotic hosts. This invention then provides a molecular, biochemical instrument whereby the dephosphorylation of tyrosine—a critical regulatory step in the mechanism of cell growth, differentiation and oncogenesis—can be specifically addressed in the context of bone maturation and repair and during select stages in the process of spermatogenesis.

The OST-PTP of the present invention is further characterized as a unique 1711 amino acid protein containing an extracellular domain of 1068 amino acids including a 17 amino acid signal sequence associated with ligand binding and 10 fibronectin type III-like domains (FN-III) which mediate cell-cell homophilic binding and cell-matrix heterophilic attachment. The intracellular region consists of a 610 amino acid cytoplasmic domain but is unusual for the protein tyrosine phosphatase (PTP) class of molecules in that two, typical cytoplasmic PTP domains are present but the active site of domain two lacks the invariant cysteine required for catalysis.

The invention is described as a 5455 base nucleotide sequence for a full length cDNA encoding the is OST-PTP protein in a single open reading frame yielding a low abundance RNA transcript of 5800 bases. The nearest homologues to the full-length OST-PTP cDNA are human PTP-$\delta$, PTP-$\gamma$ and LAR (leukocyte common antigen related protein) with 27–30% sequence identity. The invention also includes the OST-PTP nucleotide sequence in the form of an expression vehicle as well as prokaryotic and eukaryotic hosts transformed with the DNA encoding the complete OST-PTP molecule or a part of it.

Another aspect of the present invention is a native, synthetic or recombinant molecule of OST-PTP which exhibits all or a portion of the structure and properties exhibited by the native protein such as 1) a consensus PTP catalytic domain and the enzymatic capacity to selectively dephosphorylate a tyrosine phosphorylated substrate, and/or 2) the extracellular FN-III repeat motif associated with intercellular aggregation between osteoblasts and other cell types in the osteogenic matrix and with aggregation of the germ cells with basement membrane and Sertoli cells during spermatogenesis. Thus, functionally equivalent molecules, including truncated forms (analogues, variants, derivatives, and fragments-see Definitions), are considered embodiments of the present OST-PTP invention that exhibit the biological properties, or a portion of those properties, attributed to the parent OST-PTP protein. It has been demonstrated that 1) a glutathione-S-transferase fusion protein incorporating the OST-PTP catalytic region exhibits tyrosine phosphatase activity and substrate specificity, and 2) a truncated, inactive splice variant termed OST retains only the transmembrane and extracellular domains of OST-PTP but is osteoblast specific. Thus, other important embodiments of the present invention include, but are not restricted to, the GST-OST fusion protein and the OST splice variant as derivatives of the parent OST-PTP protein.

Included in the present invention is a method for preparing the OST-PTP protein, or a functional derivative, by culturing a host capable of expressing the protein and from which the protein can be expressed, recovered and purified.

Included in the present invention is any polyclonal, monoclonal or chimeric antibody specific for the OST-PTP protein or a portion of the OST-PTP molecule. This provision extends to immunoconjugates targeted at osteogenic tissue through specificity for an epitope within the OST-PTP molecule.

Also included in this invention is any chimeric molecule which contains a region which will bind to OST, i.e., an antibody or ligand, as well as a region containing a bone-specific or testis-specific agent, for example, an agent which can regulate bone remodeling. Bone-specific therapeutic agents within the present invention include, but are not limited to, any agents which are useful in the bone-related therapies or other treatments including, but not limited to, anti-tumor agents, those agents which stimulate bone growth or which block bone resorption, including inhibitors or activators of PTPases, cytokines and growth factors which are known to work on bone, such as IGF-1 and bone morphogenetic proteins. Testis-specific agents contemplated by the present invention include, but are not limited to, cytokines or activators or inhibitors of PTPases or factors that are steroidogenic agonists or antagonists or anti-tumor agents, such as M-CSF, TNFα or TGFβ.

Abnormal levels of the OST-PTP receptor/enzyme system may be detected by methods directed at determining the presence of or measuring the quantity of OST-PTP in a cell or in a subject. The present invention includes use of an antibody specific for an epitope of OST-PTP to contact a target cell or cell extract. The presence of OST-PTP or the quantity of the molecule is detected by antibody binding or quantitative assay of the amount of bound antibody.

The OST-PTP invention contains a receptor-like domain which enables the native protein to function as a transmembrane receptor involved in the process of osteogenesis. Consequently, OST-PTP can serve as a novel affinity probe for the screening of naturally occurring ligands from a biological preparation or synthetic chemical compounds directed at modification of bone growth and differentiation including treatment of metabolic bone disorders such as osteoporosis, osteopetrosis and Paget's Disease. The present invention includes methods for identifying and isolating a compound capable of binding to OST-PTP or a portion thereof such as the OST splice variant. This process involves attaching the OST-PTP molecule, or the ligand-binding domain, to a solid phase matrix and allowing the compound to bind, subsequently washing away unbound material and eluting and isolating the ligand.

Compounds with the ability to stimulate or inhibit OST-PTP activity may serve as therapeutic agents in the treatment of aberrant bone growth as well as metabolic bone diseases. Therefore, the present invention includes methods for identifying compounds capable of altering the enzymatic activity of the OST-PTP molecule. This process involves presentation of the test compound to active OST-PTP in pure form, in a membrane preparation, or in whole cells. After sufficient incubation at appropriate conditions, the enzymatic activity of the test mixture is measured for comparison with the same OST-PTP preparation assayed in the absence of that compound.

OST-PTP expression follows a highly regulated spatial and temporal pattern during osteogenesis and spermatogenesis. Abnormal expression patterns of OST-PTP or the expression of aberrant OST-PTP may be diagnostic of developmental bone disorders or susceptibility to oncogenic transformation. The present invention includes methods for detecting the presence of nucleic acids encoding normal or mutant OST-PTP in a subject. Oligonucleotide probes derived from various portions of OST-PTP can be used to test a subject for the presence of RNA encoding the protein sequence specific to the OST-PTP enzyme. A preferred probe would be one directed to the nucleic acid sequence of at least 5 amino acid residues of the invention. Northern analysis is used to measure OST-PTP mRNA levels in a cell or tissue preparation which is then quantitated by comparison to a loading control such as the RNA for a constitutively expressed message. This technology then provides a basis for comparison of RNA expression levels from normal subjects and patients with potentially altered OST-PTP levels. Moreover, it affords the opportunity to screen for the presence of mutated OST-PTP forms associated with bone disorders which may bind to a panel of preferred OST-PTP probes with different stringencies or at different molecular weights than the OST-PTP of the present invention. Correlation of mismatches with incidence of tumorigenesis may provide an important predictor of bone cancer risk.

The present invention is thus directed at a unique OST-PTP protein and its derivatives in purified, synthetic and recombinant forms. The purview of this invention includes expression restricted to bone tissue and the seminiferous tubules and extends to the properties of this molecule including 1) its catalytic capacity to dephosphorylate a tyrosine phosphorylated substrate and 2) the cell adhesive and communication properties mediated through the extracellular fibronectin-like repeats. The restricted expression pattern of this molecule to bone and testis designates it as a vehicle by which those tissues may be targeted for diagnostic or therapeutic purposes. Moreover, the regulation of OST-PTP by naturally occurring endogenous hormones such as parathyroid hormone suggests that OST-PTP levels can be used directly as an index of normal bone development and remodeling as well as normal spermatogenesis.

DESCRIPTION OF SEQUENCE LISTING

Figure 1:
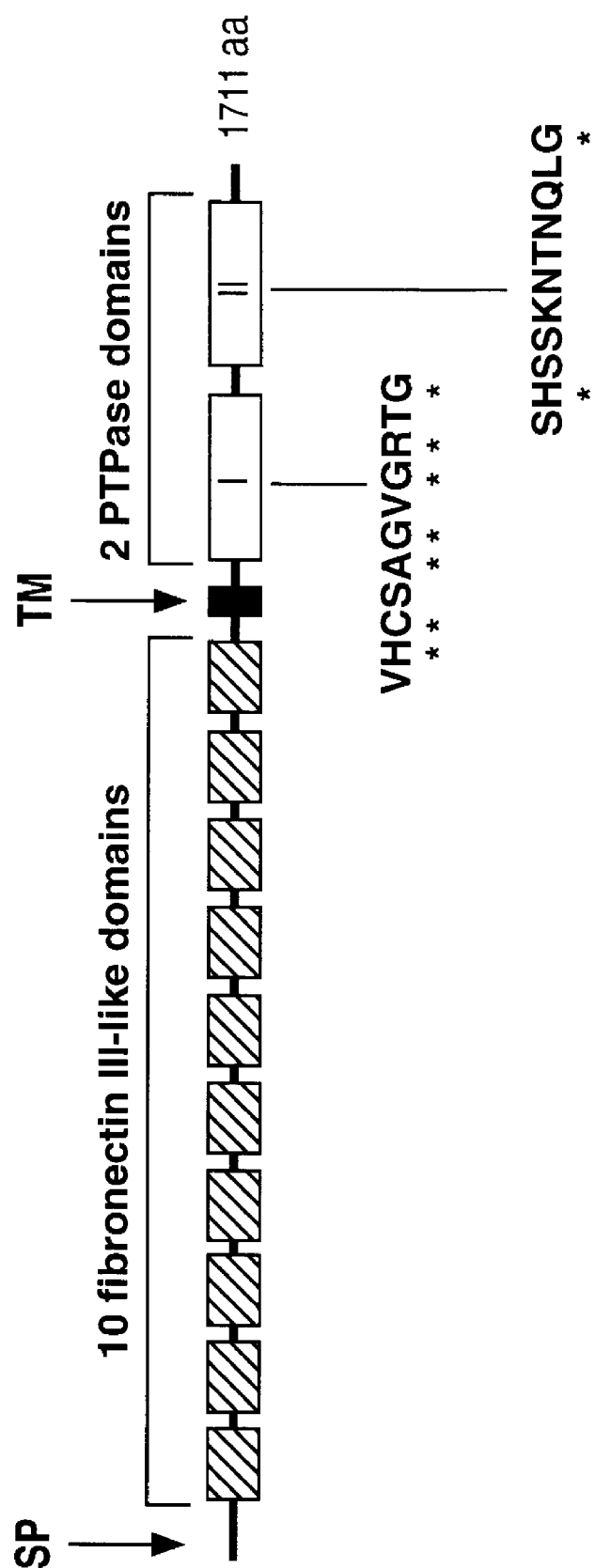
FIG. 1 (SEQ ID NO:4 and SEQ ID NO:5) is a schematic depiction of the 1711 amino acid (aa) OST-PTP protein of the present invention containing a 1068 aa extracellular domain. Important structural components include the signal peptide (SP=17 aa), the ten fibronectin type III-like domains (FN-III), the transmembrane domain (TM) and the two intracellular domains associated with phosphatase catalytic activity (PTPase domains I and II). The listed 11 amino acid sequences delineate the characteristic conserved residues at the active site but the substitutions in Domain I—specifically the cysteine to serine substitution—render it inactive (Abbreviations for the amino acid residues are: A, Ala; C, Cys; G. Gly; H. His; K, Kys; L, Leu; N, Asn; Q, Gln; R, Arginine; S, Ser; T, Thr; V, Val.). Invariant residues are indicated with an asterisk.
Figure 2:
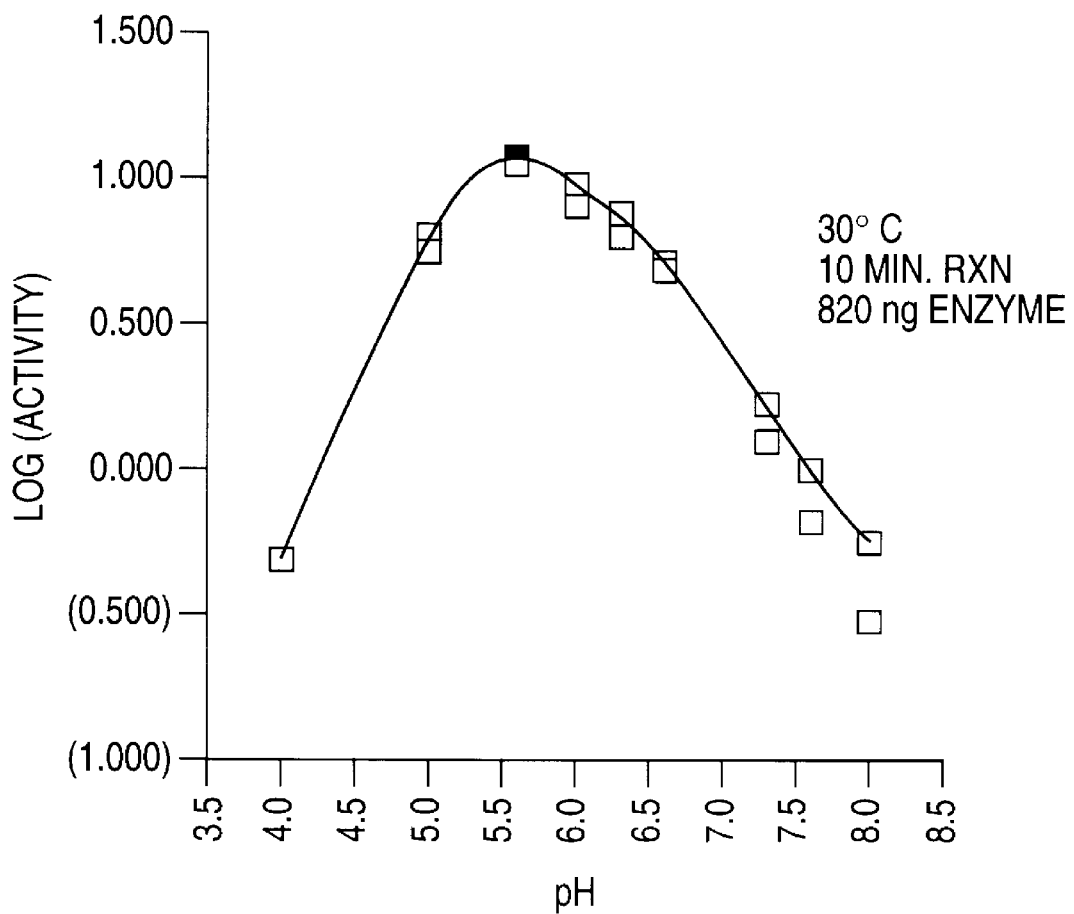
FIG. 2 presents the results of a basic kinetic analysis of the catalytic portion of the OST-PTP protein expressed as a glutathione-S-transferase fusion protein. Hydrolysis of the artificial substrate para-nitrophenylphosphate (pNPP) was determined by absorbance measurement at a wavelength of 410 nm. Enzyme activity was measured in a 200 μl reaction containing buffer (0.1M imidazole, 0.1 mM EDTA, 0.1% β-mercaptoethanol) 20 mM pNPP and 820 ng of enzyme. Incubation was performed over a range of pH at 30° C. for 10 minutes and maximum activity was detected at pH 5.5.

The Sequence Listing (SEQ ID NO.: 1) and SEQ ID NO:2) at the end of the Specification is the nucleotide sequence of cDNA together with the deduced amino acid sequence encoding OST-PTP. DNA sequencing was performed using an Applied Biosystems automated DNA sequencer. Numbers on the right of the columns indicate base positions. The first base position corresponds to the first nucleotide in the 5' extension clone #20. The ten fibronectin type III-like domains (FNI-FNX) are located as follows (for the purposes of these listings, the first amino acid listed begins the segment and the final amino acid listed terminates it): FNI=amino acid (aa) 32 (Arg) to aa 124 (Ala); FNII=aa 125 (Arg) to aa 215 (Trp); FNIII=aa 216 (Thr) to aa 303 (Trp); FNIV=aa 304 (Thr) to aa 392 (Ala); FNV=aa 393 (Ala) to aa 470 (Tyr); FNVI=aa 471 (Thr) to aa 562 (Cys); FNVII=aa 563 (Thr) to aa 652 (Gly); FNVIII=aa 653 (Trp) to aa 741 (Trp); FNIX=aa 742 (Thr) to aa 830 (Ser); and FNX=aa 831 (Val) to aa 921 (Ser). The two predicted hydrophobic domains are boxed from aa 3 (Pro) to aa 18 (Ala) and from aa 1082 (Leu) to aa 1104 (Leu). The 5' hydrophobic region demonstrates homology to a signal sequence. A predicted cleavage site is located between aa 18 (Ala) and aa 19 (Glu) as indicated by an arrow. The 3' hydrophobic end is the putative transmembrane domain. The catalytic includes aa 1348 (Val) to aa 1359 (Thr) and is 3' to the transmembrane domain, in the cytoplasmic region. A second catalytic domain which is missing key amino acids required for activity is located from aa 1668 (Val) to aa 1678 (Leu). The predicted N-linked glycosylation sites include aa 117 to aa 119 (Asn-Val-Thr), aa 239 to aa 241 (Asn-Ser-Ser), aa 259 to aa 261 (Asn-Thr-Thr), aa 431 to aa 433 (Asn-Ile-Ser), aa 551 to aa 553 (Asn-Leu-Ser), aa 570 to aa 572 (Asn-Leu-Ser), aa 620 to aa 622 (Asn-Phe-Ser), aa 649 to aa 651 (Asn-Ala-Thr), aa 663 to aa 665 (Asn-Val-Thr), aa 737 to aa 739 (Asn-Val-Ser), aa 851 to aa 853 (Asn-Trp-Thr), aa 882 to aa 884 (Asn-Thr-Ser), aa 970 to aa 972 (Asn-Met-Thr), aa 982 to aa 984 (Asn-Tyr-Thr), aa 1266 to aa 1268 (Asn-Ser-Thr), and aa 1569 to aa 1571 (Asn-Thr-Thr). The termination codon is at 5340 and the 3' noncoding sequence are included with the poly (A) tract beginning at nucleotide 5449.

MODES OF CARRYING OUT THE INVENTION

Utilizing recombinant DNA technology, the inventors identified a unique mammalian (rat) bone-testis tyrosine phosphatase protein termed osteotesticular protein tyrosine phosphatase (OST-PTP) and a truncated derivative (OST). The reverse transcriptase-polymerase chain reaction methodology was employed using degenerate primers based on the conserved regions of previously characterized tyrosine phosphatase catalytic domains. Osteogenic tissue was screened to resolve the novel OST-PTP clones from among other tyrosine phosphatase proteins. Sequence analysis including Genebank comparisons established that the nearest homologue to the OST-PTP sequence was PTP-ε, which exhibited only 45% identity in the catalytic region. Further unusual characteristics of OST-PTP are its low abundance RNA and the presence of a single active carboxy-terminus catalytic domain, in contrast to the bipartite active catalytic domains found in 14 of the 16 transmembrane PTP molecules isolated thus far. The protein also contains an extracellular domain of 10 FN-III repeats, a motif known to be important in homophilic binding of cells as well as in the attachment of cells to an extracellular matrix. These structural features and the restricted expression pattern of OST-PTP distinguish this protein as a previously undiscovered member of the protein tyrosine phosphatase family.

OST-PTP expression increases markedly (5–8 fold) in association with osteoblast differentiation and the bone mineralization, in contrast to the low levels expressed during the osteoblast proliferation. Moreover, OST-PTP expression in vitro is exquisitely sensitive to parathyroid hormone (PTH), a critical modulator of bone metabolism in vivo which inhibits osteoblast proliferation and stimulates bone resorption. Stimulation of the protein kinase A (PKA) pathway using the cyclic AMP analogue, chlorophenylthio-cAMP resulted in an increase in OST-PTP mRNA levels comparable to PTH treatment and consistent with the idea that OST-PTP is modulated by PTH through the PKA pathway. These findings indicate that the OST-PTP program is critical to proper bone growth and metabolism and, therefore, an important potential target for manipulation of bone growth, mineralization and treatment of bone pathology. The discrete timing and spatial expression pattern of OST-PTP provides a basis for targeting pharmacological agents with the capacity to alter major pathways involved in osteogenesis and maintenance of bone integrity. The transmembrane receptor structure of the OST-PTP protein suggests that ligands in the extracellular environment control the activity of this phosphatase and supports its potential role as a tissue specific target for pharmacological agents. A variety of proven methods are presently available for the purpose of screening for natural or synthetic ligands. These methods are outlined below.

(a) By attaching intact OST-PTP or its ligand-binding domain to a solid phase matrix, an affinity probe is created for screening of biological products or chemical agents to determine their capacity to interact with (i.e., bind to) the receptor of the invention. Bound material can then be eluted from the affinity probe in purified form. Methods for coupling of peptides and proteins to a solid phase matrix and means for elution are well known to those of skill in the art. Note that this technique may be applied separately to the truncated OST receptor molecule which contains the extracellular domain of OST-PTP. Furthermore, secondary screening analysis may be used to test the effect of systematic deletions or mutations in regions of the OST-PTP protein perceived to be critical to biological function. Standard recombinant technology will be used to identify, alter and characterize such mutations in previously identified ligand binding sequences deemed critical.

(b) OST-PTP or active derivatives can be used for testing of compounds to determine their ability to enhance or inhibit phosphatase activity. Modification of phosphatase activity can be assayed in vitro by addition of test compounds to purified OST-PTP or an enzymatically active derivative followed by standard enzymological analysis well known to those of skill in the art. This technology applies as well to testing of antibodies for binding and correlative antagonist or agonist properties. This assay may be performed in the presence of a known activator of OST-PTP or in the presence of an activator tyrosine kinase.

(c) The action of a compound on OST-PTP can be measured in whole cell preparations using live or fixed cells, e.g., isolated primary cells or cell lines including primary rat osteoblasts or UMR106 osteosarcoma cells which express high levels of OST-PTP under regulated conditions. A test compound is incubated with the cells and the amount of cellular phosphotyrosine is then measured according to established methods (Margolis et al., 1989, *Cell* 57:1101–1107) for comparison with cultures treated identically but lacking the test compound. In addition, this method is useful for determining whether test compounds act via the extracellular receptor portion of the OST-PTP protein. This assay may be performed in the presence of a known activator of OST-PTP or in the presence of an activator tyrosine kinase.

(d) Alternatively, method (c) can be employed with a cellular membrane fraction containing high levels of OST-PTP, e.g., primary cells or osteogenic cell lines or from transfection of cells with constructs designed to yield high levels of membrane integrated OST-PTP such as transfected COS or NIH-3T3 cells. The use of a membrane fraction allows one skilled in the art to screen compounds for action directed at the extracellular receptor portion versus the cytoplasmic enzymatic subunit. This assay may be performed in the presence of an activator of OST-PTP or the presence of an activator tyrosine kinase.

(e) The methods described above, i. e., whole cell or membrane preparations, may be applied to examine the role of the FN-III domain in cellular aggregation and differentiation. The role of the FN-III domain in intercellular aggregation and communication may be tested directly by systematic and sequential deletion of regions of the FN-III domains and analyzing their effects in primary culture or cell lines during proliferation and differentiation phases. In conjunction with these studies, drugs or antibodies previously screened as targeting the extracellular FN-III domain may be tested for effects on either inhibition or stimulation of cell adhesion and subsequent effects on cellular differentiation both in the process of osteogenesis and spermatogenesis.

(f) The OST-PTP invention may be utilized to determine the relationship between the FN-III extracellular domain and the enzymatic capabilities of the OST-PTP protein. Deletion of the extracellular ligand binding region or the use of drugs or antibodies which block the signal sequence allow analysis of phosphatase activation via the remaining extracellular region particularly the FN-III repeat domain. DNA constructs incorporating modifications of the extensive FN-III domains may be generated, transfected and expressed in transient or stable primary cells or cell lines to assay for effects on catalytic activity in combination with or separate from a role in cellular aggregation.

In summary, the cloning of OST-PTP including the OST receptor form of the invention provides a novel tool with which to screen naturally occurring ligands as well as natural or synthesized pharmacological agents with the potential for therapeutic application to a variety of bone disorders. The unique tissue specificity of the invention defines a distinct drug target while eliminating potential side effects in other tissues. Furthermore, useful chimeric molecules can be constructed which contain an OST binding region, e.g., either an anti-OST antibody or a ligand for OST, as well as a region which can modulate the process of bone remodeling or spermatogenesis. This technology has recently been utilized to design tissue specific pharmaceutical agents where a tissue specific receptor—other than bone or testis—provides the target (Trail et al., 1993, *Science* 261:212–215) in a manner analogous to that described for the present invention. Consequently, the present invention will allow this technology to extend to the process of osteogenesis as well as bone disorders such as osteoporosis, osteopetrosis and Paget's disease.

Recent evidence indicates that protein tyrosine phosphatase activation provides a counterregulatory mechanism to inhibit mitogenic influence on cells mediated through tyrosine kinase growth factor receptors, e.g., epidermal growth factor (EGF), fibroblast growth factor (FGF) and platelet-derived growth factor (PDGF). Consequently, reduced or blocked phosphatase function is implicated in the process of oncogenic transformation of cells and susceptibility to cancer. Specifically, mutation of the OST-PTP genomic DNA or mutation or dysregulation of the OST-PTP receptor/enzyme system at the RNA or protein level may play a role in development of bone-related cancers. The present invention provides methods for analysis of the genomic sequence encoding the OST-PTP invention and for evaluating or level of normal or aberrant OST-PTP RNA or protein expression which may predict or diagnose bone pathologies including cancer.

Analysis of the organization and structure of the genomic DNA encoding the OST-PTP invention can be performed by standardized procedures including but not restricted to Southern blotting (Southern, E., 1975, *J. Mol. Biol.* 98:503–517). High molecular weight genomic DNA is purified, cleaved with a variety of restriction enzymes, fractionated via agarose gel electrophoresis and transferred to a filter or membrane for hybridization with a series of OST-PTP specific probes of either purified RNA, cloned cDNA or short synthetic oligonucleotides. A preferred oligonucleotide probe would be one directed to the nucleic acid sequence of at least 5 amino acid residues of the invention. The resulting pattern of bands obtained after hybridization and stringent washing delineate the number and size of the DNA fragments containing OST-PTP sequences. These data are used to generate a restriction map of the OST-PTP gene and for comparative analysis of DNA samples from a variety of normal subjects and those with identified bone pathologies. Aberrant restriction patterns on Southern blots allow detection of deletions or rearrangements which may be associated with particular bone pathologies or serve as a predictor of bone disorders or susceptibility to bone cancer.

Analysis of RNA size and expression pattern can be performed by standardized procedures, including but not restricted to Northern blotting. Analogous to Southern blotting, total or polyadenylated RNA is purified, size-separated via agarose electrophoresis, transferred to a solid matrix and sequentially hybridized to a panel of OST-PTP cDNA or oligonucleotide probes as well as a standard probe for a constitutively expressed RNA as a loading control, e.g., alkaline phosphatase, glyceraldehyde 3-phosphate dehydrogenase or β-cytoplasmic actin. OST-PTP mRNA expression levels in a particular cell or tissue preparations from multiple subjects can then be quantified by comparison to the expression of the constitutively expressed loading control. This technology then provides a means for comparison of RNA expression levels among multiple samples to establish normal levels as well as define altered OST-PTP levels or patterns of expression. Moreover, this analysis provides a screening mechanism to detect modified or aberrant RNA products associated with bone pathologies.

These screening methods can be used even with very small amounts of DNA or RNA obtained from an individual, following use of selective amplification techniques known to those of skill in the art. Recombinant DNA methodologies capable of amplifying purified nucleic acid fragments have long been recognized including the introduction of the nucleic acid fragment into a DNA or RNA vector, the clonal amplification of the vector, and the recovery of the amplified nucleic acid fragment (Cohen et al. (U.S. Pat. No. 4,237,224); Sambrook et al., Molecular Cloning: A Laboratory Manual (Cold Spring Harbor Press, Cold Spring Harbor, N.Y., 2d ed., 1989)). Moreover, the polymerase chain reaction (PCR) provides a standardized method for selectively increasing the concentration of a particular nucleic acid even when that sequence has not been previously purified and is present only in a single copy in a particular sample (Mullis et al., 1986, *Cold Spring Harbor Symp. Quart. Biol.* 51:263–273; Erlich et al., EP 50,424; EP 84,796; EP 258,017; EP 237,362; Mullis, K., EP 201,184; Mullis et al., U.S. Pat. No. 4,683,202; Erlich, H., U.S. Pat. No. 4,582,788; and Saiki et al., U.S. Pat. No. 4,683,194).

The PCR method involves the use of two oligonucleotide probes to serve as primers for the template-dependent, polymerase mediated replication of a desired DNA sequence. Where RNA is the initial starting substrate, the enzyme reverse transcriptase is used to produce cDNA copies of each mRNA for PCR amplification and analysis. The precise nature of the two oligonucleotide primers of the PCR method is critical to the success of the method as it is the primers which define the sequence to be amplified. The oligonucleotide sequences of the probes of the PCR are selected such that they contain sequences identical to, or complementary to, sequences which flank the particular nucleic acid sequence whose amplification is desired. Therefore, the present invention is critical as it provides novel OST-PTP sequences to serve as PCR primers to exclusively amplify regions of the OST-PTP genomic DNA or RNA. Thus, by permitting cycles of polymerization, and denaturation, a geometric increase in the concentration of the desired OST-PTP sequence can be achieved (Saiki et al., 1985, *Biotechnology* 3:1008–1012; and Mullis et al., 1987, *Meth. Enzymol.* 155:335–350). As described for Southern and Northern analysis, the OST-PTP PCR products can be analyzed to detect rearrangements or deletions associated with bone pathology. Multiplex PCR involving simultaneous amplification of a constitutively expressed transcript as well as the OST-PTP sequence allows quantitative analysis to be performed by normalizing OST-PTP expression level on the basis of the constitutive product level. Comparisons of normalized expression levels then can be made among subjects for correlation with bone pathology.

The present invention provides methods for evaluating the level of normal or mutant OST-PTP both as a functional enzyme and based on molecular weight. The presence of normally functioning OST-PTP in a subject can be tested using direct enzymatic assay for the tyrosine phosphatase activity. Such biochemical measurements can be performed in vitro using purified enzymes which allow precise measurements of enzyme activity, or with membrane preparations, or whole cells, where the net phosphotyrosine level is determined. In addition, a polyclonal or monoclonal antibody specific to the OST-PTP invention may be used to characterize the molecular weight of the OST-PTP protein using a standardized technique of Western blotting. Protein is separated by electrophoresis using a sodium dodecyl sulfate polyacrylamide gel and then transferred to a filter for hybridization with an OST-PTP specific antibody. Variations in the molecular weight of the OST-PTP protein associated with mutations or post-translational modification can be detected by this technique for correlation with bone pathology.

The antibodies useful in the present invention may be employed histologically, as in immunofluorescence or immunoelectron microscopy, for in situ detection of OST-PTP expression. In situ detection may be accomplished by removal of a histological specimen from a subject for incubation with the OST-PTP specific antibody which may be detected by any of a number of techniques well-known in the art. Through the use of such a procedure, it is possible to determine not only the presence of OST-PTP but also its distribution throughout the biological sample. Thus OST-PTP may be an important diagnostic tool in analysis of bone development and a hallmark of certain bone disorders.

It will be appreciated that delineation of the nucleotide and amino acid sequences and general structural domains of the OST-PTP molecule allows one skilled in the art to generate a biological equivalent of this protein using readily available RNA in vitro translation systems or through biosynthetic peptide assembly systems. Moreover, truncated molecules expressing one or a portion of the functional attributes of the parent OST-PTP can be generated by utilizing partial or modified nucleotide and/or amino acid sequence information. Such truncated OST-PTP versions borrowing on the features of the present invention can, in principle, eventually recover the biological properties of native OST-PTP without necessarily utilizing the exact sequence as disclosed. For example, in one embodiment, the inventors constructed an enzymatically active fusion protein from the catalytic portion of OST-PTP and glutathione-S-transferase using a bacterial expression vector. In another embodiment of the invention, the minimal ligand binding sequence can be defined and similarly incorporated into truncated OST-PTP mini-gene constructs adding ligand specificity to catalytic activity of expressed proteins. Likewise, identification of tissue specific regulatory elements associated with OST-PTP expression will provide another important incremental step in assembly of the OST-PTP molecule. Thus, the present invention provides the necessary framework for the parsimonious dissection of OST-PTP nucleotide sequence to derive the minimal functional mini-gene construct for therapeutic and diagnostic applications. The product of such dissection is considered to be a derivative of OST-PTP inasmuch as it yields a protein with the biological characteristics described for OST-PTP and utilizes regions of sequence homologous to OST-PTP in order to obtain those characteristics. These definitions are specifically clarified as follows:

The invention provides the naturally occurring molecule "substantially free of other proteins or glycoproteins." It will be understood that the mammalian OST-PTP protein of the present invention can be biochemically purified from a variety of cell or tissue sources including primary cells and cell lines by standard protein purification techniques well known to those of skill in the art. "Substantially pure" indicates that the protein has been purified away from at least 70 percent (on a weight basis), and from even at least 99 percent if desired, of other proteins and glycoproteins with which it is natively associated, and is therefore substantially free of them.

In another embodiment, the invention is directed to a recombinant mammalian OST-PTP protein. The recombinant DNA molecules of the present invention can be produced through any of a variety of means, such as, for example, DNA or RNA synthesis, or more preferably, by application of recombinant DNA techniques. Techniques for synthesizing such molecules are well known to those of skill in the art (Wu et al., 1978, *Prog. Nucl. Acid. Res. Molec. Biol.* 21:101–141). Because the gene for the OST-PTP protein can be isolated or synthesized, the polypeptide can be synthesized substantially free of other proteins or glycoproteins of an origin in a prokaryotic organism or in a non-mammalian eukaryotic organism, if desired. As intended by the present invention, a recombinant OST-PTP molecule produced in mammalian cells, such as transfected COS, NIH-3T3, or CHO cells, for example, is either a naturally occurring protein sequence or a functional derivative thereof. Where a naturally occurring protein or glycoprotein is produced by recombinant means, it is provided substantially free of the other proteins and glycoproteins with which it is natively associated.

In a further embodiment, the invention provides "functional derivatives" of OST-PTP. By "functional derivative" is meant a "fragment," "variant," "analog," or "chemical derivative" of the OST-PTP molecule, which terms are defined below. A functional derivative retains at least a portion of the function of the OST-PTP, such as binding to a specific antibody, phosphatase enzymatic activity or binding of the extracellular domain to a ligand which permits its utility in accordance with the present invention.

A "fragment" of OST-PTP refers to any subset of the molecule, that is, a shorter peptide. The term "fragment" is used to indicate a polypeptide which is derived from the OST-PTP protein or glycoprotein having a naturally occurring protein sequence by appropriately modifying the DNA sequence encoding the OST-PTP protein or glycoprotein, resulting in deletion of one or more amino acids at one or more sites of the C-terminal, N-terminal, and within the native sequence. Fragments of the OST-PTP protein or glycoprotein are useful for screening for compounds that are antagonists or agonists. It is understood that such fragments of the OST-PTP protein or glycoprotein may retain characterizing portion(s) of the native OST-PTP or glycoprotein. In particular, such fragments should retain one or more biological activities or functions which are characteristic for the intact OST-PTP proteins or glycoproteins. Examples, which are not intended to be in any way limiting to the scope of the invention claimed of OST-PTP fragments are: a) the catalytic domain; b) the signal sequence c) regions of the OST-PTP proteins or glycoproteins which interact with other molecules in the intact cell; d) the FN-III repeat extracellular domain; and e) regulatory parts of OST-PTP.

A "variant" of OST-PTP refers to a molecule substantially similar to either the entire peptide or a fragment thereof. Variant peptides may be conveniently prepared by direct chemical synthesis of the variant peptide, using methods well known in the art. Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct of OST-PTP protein or glycoprotein, provided that the final construct possesses the desired activity or function present in the intact OST-PTP proteins or glycoproteins. Examples of such activities and functions are: a) the catalytic activity; b) substrate specificity; c) interaction with other molecules in vitro and in vivo; and d) regulatory functions. Only one of such activities or functions needs to be retained after any combination of deletion, insertion, and substitution. These examples are not intended to be in any way limiting to the scope of the invention claimed. Obviously, the modifications or mutations that will be made in the DNA encoding the OST-PTP protein or glycoprotein must not alter the reading frame and preferably will not create complementary regions that could produce secondary mRNA structure (see EP 75,444).

In a further aspect, the invention provides for an OST-PTP protein or glycoprotein having additional amino acids that are derived from a naturally occurring OST-PTP protein or glycoprotein. This OST-PTP protein or glycoprotein is derived by appropriately modifying the DNA sequence encoding the OST-PTP protein or glycoprotein, resulting in addition of one or more amino acids at one or more sites of the C-terminal, N-terminal, and within the native sequence. It is understood that such an OST-PTP protein or glycoprotein having additional amino acids may retain characterizing portion(s) of the native OST-PTP protein or glycoprotein. In particular, such OST-PTP proteins or glycoproteins with additional amino acids should retain one or more biological activities or functions which are characteristic for the intact OST-PTP proteins or glycoproteins. Examples of such characteristics, of which at least one should be retained: a) the catalytic activity; b) the substrate specificity; c) interaction with other molecules in the intact cell; d) intercellular homophilic binding; and e) regulatory functions of OST-PTP. These examples are not intended to be in any way limiting to the scope of the invention claimed.

At the genetic level, these variants ordinarily are prepared by site-directed mutagenesis (Adelman et al., 1983, *DNA* 2:183) of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

An "analog" of OST-PTP refers to a non-natural molecule substantially similar to either the entire molecule or a fragment thereof.

A "chemical derivative" of the OST-PTP contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues. Derivatized moieties may improve the solubility, absorption, biological half life, and the like. The moieties may alternatively eliminate or attenuate any undesirable side effect of the protein. Moieties capable of mediating such effects are exemplified in Remington's Pharmaceutical Sciences, 16th ed., Hack Publishing Co., Easton, Pa. (1980).

In a further aspect, the invention encompasses so-called chimeric molecules which are made up of OST-PTP in which one or more specific amino acid sequences are replaced with homologous sequence(s) from another protein or glycoprotein. Chimeric molecules include, for example, an OST-PTP protein or glycoprotein having a ligand-binding extracellular domain that is grafted onto a portion of another protein or glycoprotein.

"Homologous sequences" are defined as sequences in two or more PTP proteins which are similarly positioned in the primary sequence and which may exhibit sequence homology. It should be emphasized that "homologous sequences" should not be limited to cases with high degree of homology. Chimeric molecules are important tools for elucidating structure-function relationships and for identifying specific compounds (drugs). Therefore, the most useful chimeras are often, but not always, molecules in which a certain portion of one molecule has been replaced with the similarly positioned, but divergent, sequence from another, otherwise homologous, molecule. Thus, the exchanged portions will quite often represent the parts of the molecules where they differ the most.

This invention is also directed to an antibody specific for an epitope of OST-PTP, and the use of such antibody to detect the presence of, or measure the quantity or concentration of, OST-PTP in a cell, a cell or tissue extract, or a biological fluid. The term "antibody" is meant to include polyclonal antibodies, monoclonal antibodies (mAhs), chimeric antibodies, and anti-idiotypic (anti-Id) antibodies. Polyclonal antibodies are heterogeneous populations of antibody molecules derived from the sera of animals immunized with an antigen. Monoclonal antibodies are a substantially homogeneous population of antibodies to specific antigens. MAbs may be obtained by methods known to those skilled in the art (Kohler and Milstein, 1975, *Nature* 256:495–497) and U.S. Pat. No. 4,376,110. Such antibodies may be of any immunoglobulin class including IgG, IgM, IgE, IgA, GILD and any subclass thereof.

Chimeric antibodies are molecules, different portions of which are derived from different animal species, such as those having variable region derived from a murine mAh and a human immunoglobulin constant region. Chimeric antibodies and methods for their production are known in the art (Cabilly et al., 1984, *Proc. Natl. Acad. Sci. USA* 81:3273–3277; Morrison et al., 1984, *Proc. Natl. Acad. Sci. USA* 81:6851–6855; Boulianne et al., 1984, *Nature* 312:643–646; Cabilly et al., European Patent Application 125023 (published Nov. 14, 1984); Taniguchi et al., European Patent Application 171496 (published Feb. 19, 1985); Morrison et al., European Patent Application 173494 (published Mar. 5, 1986); Neuberger et al., PCT Application WO 86/01533 (published Mar. 13, 1986); Kudo et al., European Patent Application 184187 (published Jun. 11, 1986); Morrison et al., European Patent Application 173494 (published Mar. 5, 1986); Sahagan et al., 1986, *J. Immunol.* 137:1066–1074; Robinson et al., PCT/US86/02269 (published 7 May 1987); Liu et al., 1987, *Proc. Natl. Acad. Sci. USA* 84:3439–3443; Sun et al., 1987, *Proc. Natl. Acad. Sci. USA* 84:214–218; Better et al., 1988, *Science* 240:1041–1043). These references are hereby incorporated by reference.

An anti-idiotypic (anti-Id) antibody is an antibody which recognizes unique determinants generally associated with the antigen-binding site of an antibody. An anti-Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these isotypic determinants (the anti-Id antibody).

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the OST-PTP of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the final mAb specific for a R-PTPase epitope. The anti-Id mAbs thus have their idiotypic epitopes, or "idiotopes" structurally similar to the epitope being evaluated, such as OST-PTP.

The term "antibody" is also meant to include both intact molecules as well as fragments such as Fab which are capable of binding antigen. Fab fragments lack the Fc fragment of intact antibody, clear more rapidly from the circulation, and may have less non-specific tissue binding than an intact antibody (Wahl et al., 1983, *J. Nucl. Med.* 24:316–325). It will be appreciated that Fab and other fragments of the antibodies useful in the present invention may be used for the detection and quantitation of OST-PTP according to the methods for intact antibody molecules.

In additional embodiments of the present invention, a DNA sequence encoding a OST-PTP molecule and methods for expressing the DNA sequence are provided. One of ordinary skill in the art will know how to identify and clone additional PTP molecules, of human or other mammalian species, which have sequence homology to the OST-PTP molecules described herein, using the genetic sequences and oligonucleotides of the present invention without undue experimentation. Furthermore, manipulation of the genetic constructs of the present invention allow the grafting of a particular ligand-binding receptor domain onto the transmembrane and catalytic portions of the OST-PTP resulting in chimeric molecules. Non-limiting examples of such chimeric molecules include the OST-PTP wherein the receptor is an epidermal growth factor receptor, a fibroblast growth factor receptor, and the like. Genetically engineered chimeric receptors are known in the art (Riedel et al., 1986, *Nature* 324:628–670).

Genetic constructs encoding OST-PTP, functional derivative thereof, and chimeric molecules such as those described above, can be used in gene therapy. An abnormal or dysfunctional OST-PTP, which results in disease, may be replaced by infusion of cells of the osteogenic lineage transfected with a normal OST-PTP. Alternatively, or additionally, cells carrying a chimeric OST-PTP having a receptor to a ligand of choice can be used for such gene therapy.

EXAMPLE I

Isolation of Rat OST-PTP cDNA Clones

The bone-testis specific phosphatase cDNA sequence was first identified in fetal rat calvaria and the rat osteosarcoma cell line, UMR106, messenger RNA by a reverse transcription polymerase chain reaction (RT-PCR). These two sources of bone starting material, fetal rat calvaria, and rat osteosarcoma cell line (UMR106), were chosen based on both information in the literature and availability. PCR derivation of a hybridization screening probe was accomplished utilizing three sets of degenerate oligonucleotide primers designed to amplify conserved regions within the tyrosine phosphatase catalytic regions. Three of the 5' primers corresponding to the conserved amino acids, DYINA (SEQ ID NO:6) ((5'-CAGTGGATCC(A/C/T)GA(C/T)TA(C/T)AT(A/C/T)AA(T/C)GC-3' (SEQ ID NO:7)); (72-fold degeneracy), YIATQGP (SEQ ID NO:8) ((5'-CAGTGGATCCTACAT(C/T)G(C/T)(A/C/T)(A/G)C(C/A)CA(A/G)GG-3') (SEQ ID NO:9); (96-fold degeneracy), and KCDQYW (SEQ ID NO:10) ((5'CAGTGGATCCAA(A/G)TG(C/T)(C/G)(A/C)(A/C/G/T)(C/G)A(A/G)TA(C/T)TGGCC-3') (SEQ ID NO:11); (512-fold degeneracy) were paired with a common 3' primer corresponding to the active site, HCSAGVGR (SEQ ID NO:12) ((5'-CTAGTCTAGACCNA(T/A)(T/A/G)CCNGC(A/G)CA(A/G)TG-3') (SEQ ID NO:13); (768-fold degeneracy). The 5' and 3' primers included sites for restriction enzymes BamHI and XbaI, respectively. The template for PCR reactions was first-strand cDNA synthesized using poly A+ RNA isolated from rat osteosarcoma line UMR106 and fetal rat calvaria. Total RNA was isolated using RNAzol B (Tel-Test Inc.) and the poly A+ RNA was isolated following the recommended conditions in the Poly ATtract mRNA Isolation System IV (Promega). The cDNA synthesis reactions were performed with the Invitrogen cDNA cycle kit using instructions recommended by the manufacturer. The PCR reactions included ⅕ and ⅒ volume of the original cDNA synthesis reaction and 500 ng of each primer along with the recommended reagent concentrations in the GeneAmp kit (Perkin-Elmer). The PCR conditions were: 94° C., 1 minute; 55° C., 1 minute; 72° C., 1 minute; for 35 cycles. For PCR from calvaria, reamplification of original PCR reactions was necessary to see products. Products of the expected size using the DYINA (SEQ ID NO:6) pair (495 bp) and the YIATQGP (SEQ ID NO:8) pair (432 bp) were isolated after fractionation, digested with BamHI and XbaI and cloned into the pBluescript II vector (Stratagene). Approximately 200 independent clones were sequenced using the T3 and T7 primer sites within the vector. Sequencing was done following the recommended conditions in the Sequenase sequencing kit (GibcoBRL Life Technologies).

Two rat UMR106 cDNA libraries were screened to isolate the full length clone of OST-PTP. The rat osteosarcoma cell line (UMR106) was obtained from American Type Culture Collection (ATCC) and were grown in Dulbecco's Minimal Eagle Media (DMEM), 10% fetal bovine serum (Hyclone Laboratories, Inc.), 1% glutamine (GibcoBRL Life Technologies), and 1% penicillin-streptomycin (GibcoBRL Life Technologies). The cells were discarded after the twentieth passage. One of these libraries was made from poly A+ RNA of normal confluent UMR106 cells and primed with oligo dT and random primers using the TimeSaver cDNA Synthesis Kit from Pharmacia. This kit allowed for synthesis of cDNA with NotI restriction sites flanking the cohesive EcoRI end, and facilitated cloning into the predigested Lambda ZapII vector (Stratagene) which also has cohesive EcoRI ends. The second library was a Lambda ZapII cDNA library custom made by Stratagene using poly A+ RNA from UMR106 cells stimulated with 100 nM PTH for 18 hours. The PCR fragment of OST-PTP was $^{32}$P-labeled either by random priming following the recommended conditions in the Random Primers DNA labelling kit (GibcoBRL Life Technologies) or by synthesizing a riboprobe using the procedure recommended by the manufacturer (Promega). All probes had the unincorporated nucleotides removed by using a NICK column as recommended by the manufacturer (Pharmacia). Approximately 106 plaques were plated and duplicate filters were screened by hybridization. The hybridization conditions for the filters identical to the conditions described in detail under the section on RNA analysis. Initial screens yielded incomplete, poly A-tailed clones which were 2.6 kb in length.

To obtain the 5' end, 5' Rapid Amplification of cDNA Ends (RACE) was performed using the 5'RACE system (GibcoBRL Life Technologies) as recommended by the manufacturers. Several independent clones (5 total) were synthesized and sequenced using an automated sequencer (Applied Biosystems, Inc.) and procedures recommended by the manufacturer to define the full-length clone. To verify the authenticity of the sequence, an 870 base pair probe (random-prime labeled) corresponding to one of the RACE products, was used to rescreen the custom Stratagene library.

Analysis of RNA for Expression of OST-PTP

Figure 3:
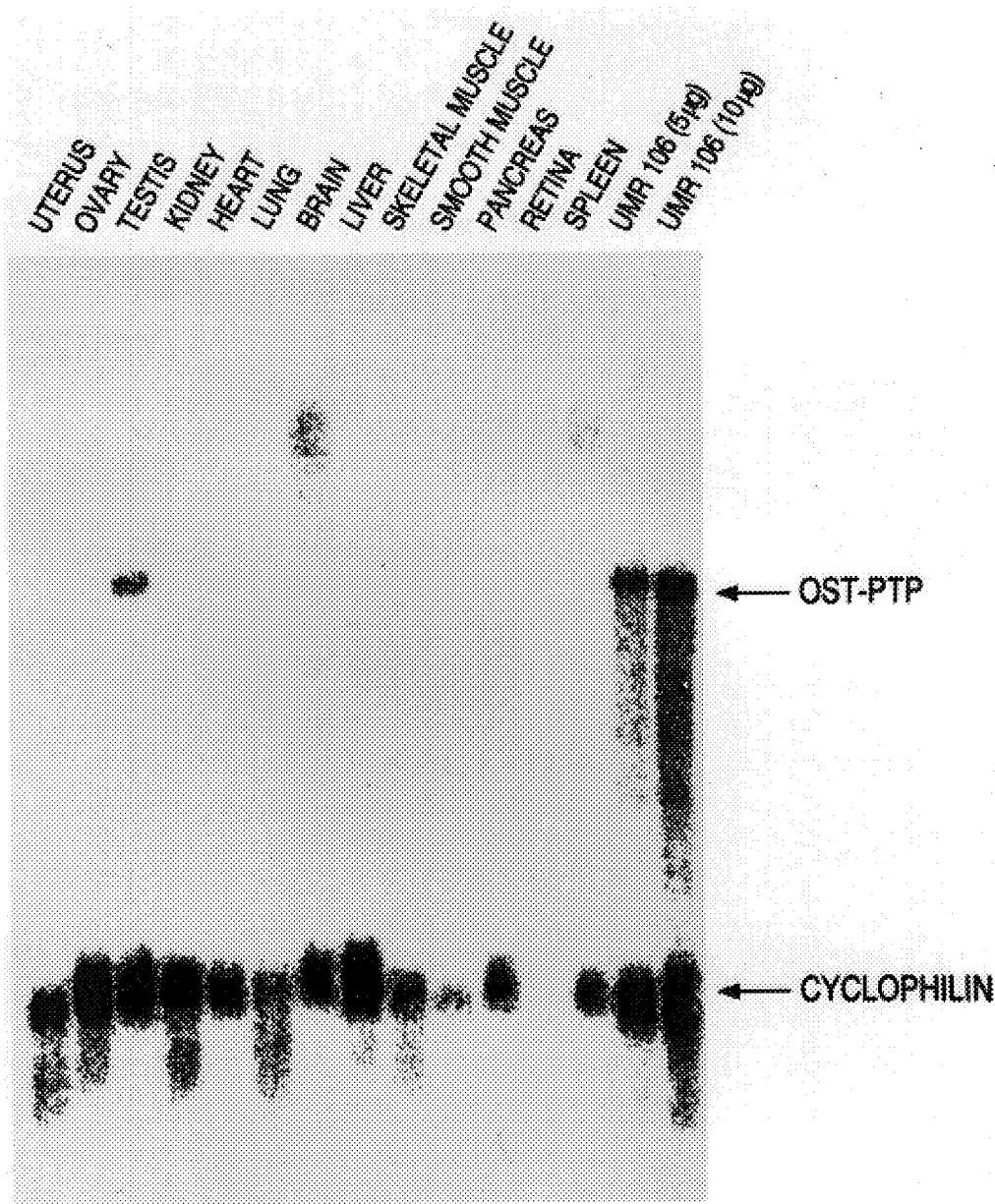
FIG. 3 is an RNA blot analysis of the expression of the novel OST-PTP transcript in various tissues of the rat and confluent cultures of the UMR 106 osteosarcoma cell line (standard for OST-PTP expression in bone). The Northern blot consisted of 10 ug of polyadenylated RNA per lane (except where indicated that 5 ug of UMR 106 RNA was loaded) fractionated on a 6.6% formaldehyde-1% agarose gel and transferred to a nylon membrane. A riboprobe corresponding to the extracellular domain of the OST-PTP transcript and a cDNA probe for cyclophilin were hybridized to the blot as an indicator of the presence of OST-PTP transcripts normalized for the amount of cyclophilin mRNA which was considered to be standard for all conditions. The results indicated that the OST-PTP transcript was exclusively expressed in RNA derived from bone cells and from testis.
Figure 4A:
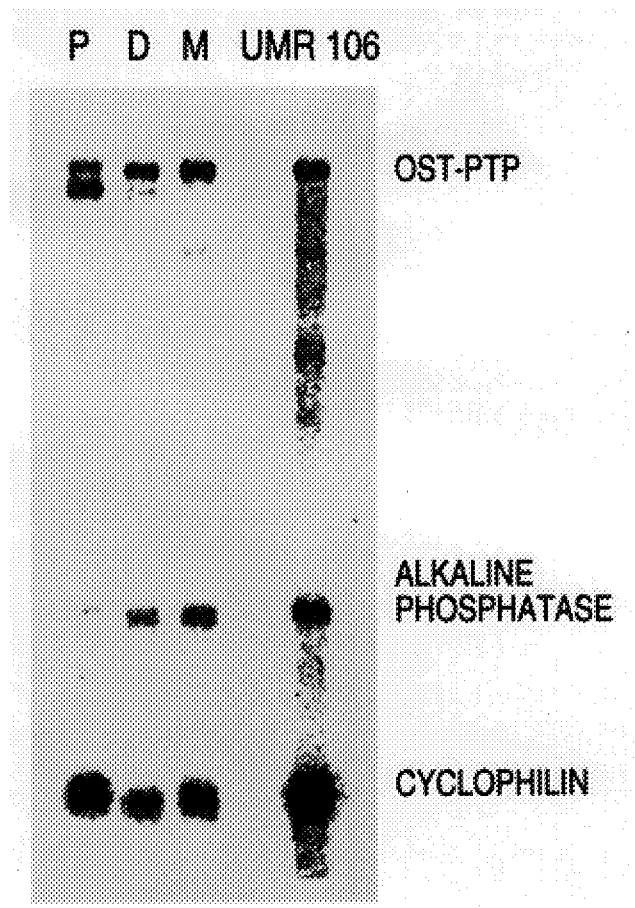
FIG. 4A is an RNA blot analysis as described in FIG. 3 with the addition of a cDNA probe for alkaline phosphatase transcripts. RNA from cultures of primary rat osteoblasts was harvested during cell proliferation (P), extracellular matrix differentiation (D) and extracellular matrix mineralization (M) and from confluent cultures of UMR 106. Note that a smaller 4.8 kb transcript termed OST which contained the extracellular domain was present in the proliferation and differentiation phases in addition to the 5.8 kb OST-PTP transcript.
Figure 4B:
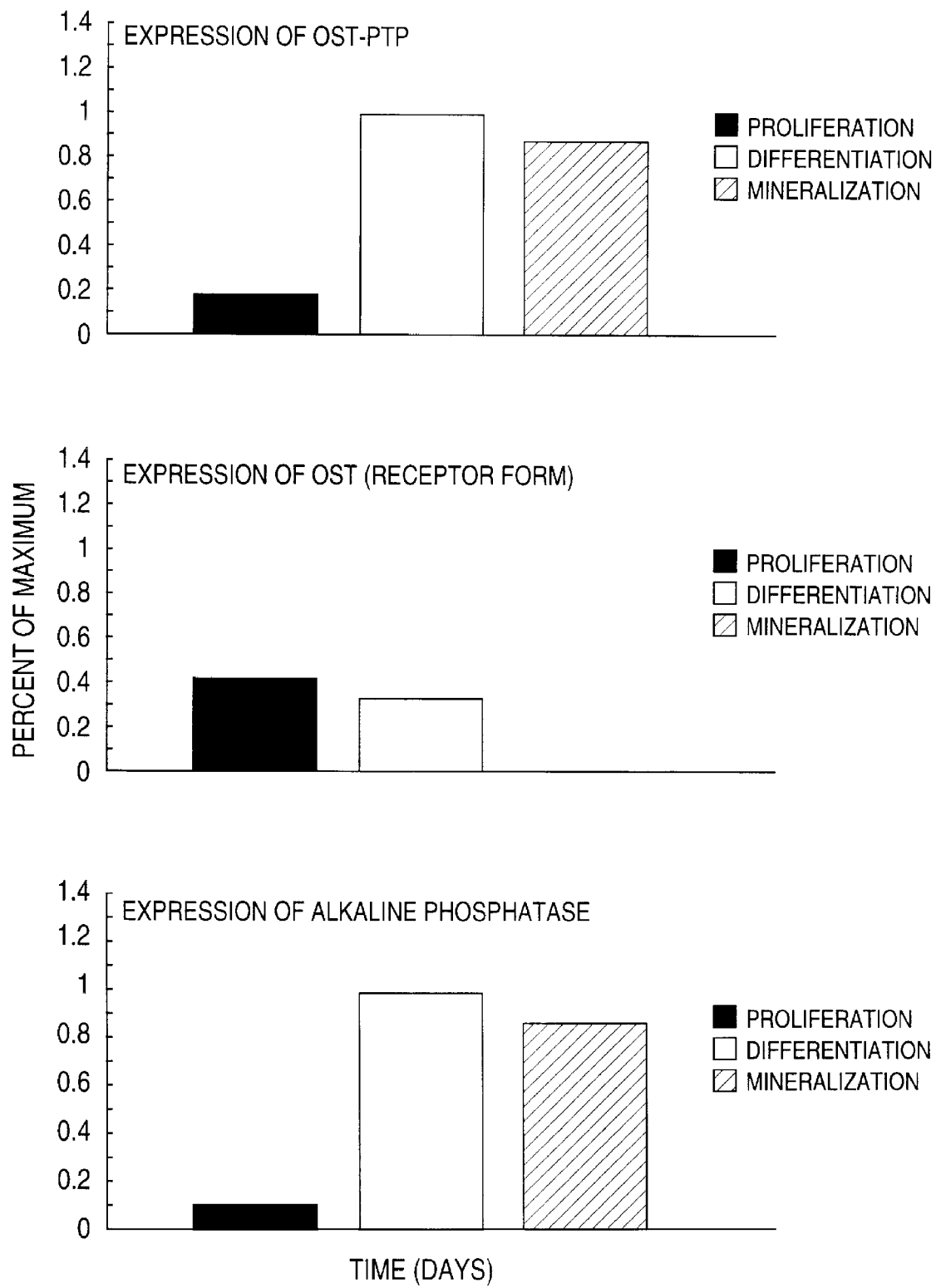
FIG. 4B is a histogram comparing expression of the OST-PTP transcript during the phases of osteoblast proliferation, differentiation and mineralization. The Northern blot in FIG. 4A was analyzed by phosphorimager scanning (Molecular Dynamics) and the results were normalized to the level of cyclophilin in each lane. OST-PTP expression was low during proliferation, increased 10 fold during differentiation and started to decline during mineralization. The 4.8 kb OST transcript was expressed at highest levels during proliferation, declined during differentiation and was absent during the mineralization phase.

RNA was analyzed by Northern blot hybridization to determine the tissue specificity of the OST-PTP clone. Poly A$^+$ RNA was extracted from an array of adult rat tissues: uterus, ovary, testis, kidney, heart, liver, lung, spleen, brain, skeletal muscle, smooth muscle, pancreas and retina. Poly A$^+$ RNA derived from UMR106 was used as a standard to control for expression in bone. The RNA preparations were quantitated by absorbance at 260 nm and, depending on the message abundance, either total cellular RNA or poly A+ RNA was electrophoretically separated in a 6.6% formaldehyde-1% agarose gel. RNA fractionated in such gels was transferred to Magnagraph nylon membrane (MSI) in 20× SSC by capillary action method. Two different types of probe; riboprobe (RNA) or random primed cDNA probe, were used depending on the experiment. The riboprobe used for hybridization corresponded to the extracellular domain of OST-PTP, and was labeled by in vitro transcription using $^{32}$P-a (3000 Ci/mM) as described by manufacturers (Promega). The DNA probes used for hybridization were rat H4 histone (Grimes et al., 1987 *Exp. Cell Res.* 173:534–545) rat type I collagen (Genovese et al., 1984, *Biochemistry* 23:6210–6216) rat type II collagen (Kohno et al., 1984, *J. Biol. Chem.* 259(22):13668–13673), rat alkaline phosphatase (Noda et al., 1987, *J. Bone and Mineral Res.* 2(2):161–164), rat osteopontin (Oldberg et al., 1986, *Proc. Natl. Acad. Sci. USA* 83:8819–8823), rat osteocalcin (Lian et al., 1989, *Proc. Natl. Acad. Sci. USA* 86:1143–1147) and cyclophilin. All DNA probes were labeled with $^{32}$P-a (3000 Ci/mM) by the Random Primers DNA labeling kit using manufacturer's recommended conditions (GibcoBRL Life Technologies). Prehybridizations and hybridizations for the OST-PTP riboprobe were performed in 50% formamide; 5× SSC; 5× Denhardts, 50 mM NaPO$_4$ buffer, pH 6.5; 1% SDS; and 250 ug/ml salmon sperm DNA at 68° C. for 16 hours. For hybridizations, 10$^6$ cpms/ml probe was added. Following hybridization, the blots were washed twice at room temperature in 1× SSC+0.1% SDS (30 minutes per wash), and then washed twice in 0.1× SSC+0.1% SDS (30 minutes per wash) once at room temperature and once at 68° C. The prehybridization/hybridization conditions for the DNA probes were the same as described above except the temperature was lowered to 43° C. For hybridization, 10$^6$ cpms/ml probe and 10% dextran sulfate were added (Maniatis et al., 1982, Molecular Cloning: a Laboratory Manual (Cold Spring Harbor Laboratory, Cold Spring Harbor, N.Y.)). The washes were done as described above. The results were visualized either by autoradiography or by scanning with a phosphorimager (Molecular Dynamics). All quantifications were normalized against the amount of cyclophilin message which was considered to be standard for any given conditions. It can be seen in FIG. 3 that the OST-PTP clone appeared to have a message size of 5.8 kb and was expressed in rat tissue only in RNA derived from bone and testis.

OST-PTP Expression During Osteogenesis

The expression of OST-PTP was further characterized by measuring its expression during rat primary osteoblast development (osteogenesis). Primary rat osteoblasts were derived from calvaria of fetal rats of 21 days gestation. The calvaria were surgically isolated, and the periosteum and suture lines removed. The calvaria were then subjected to sequential digestions of 20, 60, 90 minutes at 37° C. in 2 mg/ml collagenase B (Boehringer Mannheim, Lot# EHA131)/0.25% trypsin (GibcoBRL Life Technologies). (This procedure is a modification of Aronow et al., 1990, J. Cell Physiol. 143:213–221). The cells in the first digest were discarded, while those released from the other two digests were pooled for plating in minimal essential media (GibcoBRL Life Technologies) supplemented with 10% defined fetal bovine serum (Hyclone Laboratories, Inc., Lot# 11112275), and 1% penicillin-streptomycin-amphotericin B (GibcoBRL Life Technologies), in 75 cm$^2$ flasks at a density of 1×10$^6$ cells. The total yield of cells ranged from 3 to 5×10$^6$ per pregnant rat. After 24 hours the media was changed and cell viability ranged from 90–95%. At confluence (day 5), the cells were cultured in BGJb media (GibcoBRL Life Technologies) supplemented with 10% defined fetal bovine serum, 1% penicillin-streptomycin-amphotericin B, 50 ug/ml ascorbic acid, and 10 mM α-glycerol phosphate.

Cellular RNA was isolated at various times during the differentiation time course (5, 7, 9, 11, 13, 15, 17, 19, 21, 23, 25, 27, 29, 31 and 33 days) and assayed for the steady state levels of various transcripts by Northern blot analysis. The cells were initially characterized using a series of markers of is osteoblast differentiation, including probes for the extracellular matrix-associated gene, type I collagen, and the osteoblast phenotype marker genes, osteopontin, osteocalcin, and alkaline phosphatase. The time of maximal expression of phenotypic markers of the 33 day developmental sequence did not vary by more than 48 hours in independent experiments using the standardized lots of culture reagents as described above. The results were quantitated by Phosphorimager scanning and normalized to cyclophilin expression to derive the maximal expression level for each transcript.

The results indicated that the cells were moving through differentiation in a manner similar to that reported in the literature (Aronow et al., 1990, J. Cell. Phys. 143:213–221). The cultures formed mineralizing nodules with very little chondrocyte contamination and developed along a pathway which could be divided into three stages, proliferation (day 1–7), differentiation (day 5–29), and mineralization (day 27–33). Once the developmental pathway of the primary cells was established, Northern blot analysis was carried out to determine OST-PTP expression. Results showed that OST-PTP expression was very low during proliferation, increased 10 fold during the differentiation stage and started to decline during mineralization (2 fold). A second transcript (OST) was expressed at the highest level during proliferation, declined during differentiation and was absent during mineralization.

Tissue Distribution of OST-PTP

Based on the results of the Northern analysis, in situ hybridizations were performed with testis from adult rats to further characterize expression in that tissue. In these hybridizations unperfused testis from Sprague-Dawley rats were collected and frozen in Tissue Tek embedding medium (Miles) on dry ice. Tissue sections (10–15 Mm) were cut at −15° C. and thaw mounted on poly-L-lysine slides. Double-labeled $^{35}$S-UTP and CTP riboprobes were prepared using the Maxiscript (T3/T7/SP6) in vitro transcription kit (Ambion) with modifications to the manufacturer's protocol. The template for antisense and sense riboprobes encoded the original 470 bp PCR fragment. Hybridizations were performed as previously described with minor modifications for testis tissue (S. Watson et al., pp. 4–29, Society For Neuroscience Short Course I Syllabus (A. Sunderman, ed. , Society for Neuroscience, Washington, D.C., 1988). Sequential sections with sense probe and RNase treatment were run for each antisense section. Completed slides were dipped in Kodak photographic emulsion (NBT-2) and exposed for 14–21 days. Sections were developed and counterstained with hematoxylin-eosin (Richard Allan, Inc.). The slides were viewed and photographed on a Zeiss Axioskop with a (Micro Video Instruments, Inc.) darkfield illumination step.

These steps revealed that OST-PTP transcripts are spatially restricted to the basal portion of the seminiferous tubule, suggesting localization to the Sertoli cell and/or primary spermatogonia. It is interesting to note that this expression is stage-specific. Abundance of the OST-PTP transcripts appears greatest between stages I–VII when maturing spermatids remain buried within the Sertoli epithelium. Those tubules with low or non-detectable signals possess mature spermatids at the luminal surface of the Sertoli epithelium (stages VIII–IX) or immature spermatids with heads lacking the densely staining chromatin and the strong "bent rod" appearance (stages X–XIII). Analysis of the OST-PTP expression in neonates (day 10–18) revealed both temporal and spatial regulation of its expression within the developing seminiferous tubules.

The analysis of RNA expression by the combination of Northern blots and in situ hybridization demonstrated a restricted tissue distribution for OST and OST-PTP to bone and testis. Both tissues possess highly regulated temporal and spatial organization which is necessary for the continuous differentiation and function of specific cell populations. Within the seminiferous tubule, coupled paracrine and cell surface interactions between the Sertoli cell, germ cell and the extracellular matrix (basement membrane) are essential to spermatogenesis (see Skinner, M. K., 1991, Endocrine Rev. 12:45, and A. L. Kerszenbaum, 1994, Endocrine Rev. 15:116) in a manner analogous to the coupling of the osteoblast-osteoclast function in bone remodeling.

Consequently, in addition to its role in bone, OST-PTP also appears to function in the regulation of germ cell differentiation in the testis.

Parathyroid Hormone Treatment of UMR106 Cells

Parathyroid hormone is an important bone hormone. It has been reported to inhibit cell proliferation, and DNA synthesis, in the UMR106 cells and increase expression of proteins, such as collagenase, that potentiate the onset of resorption by osteoclasts (Scott et al., 1992, *Mol. Endo.* 6(12):2153–2159 and Clohisy et al., 1992, *Mol. Endo.* 6(11):1834–1842). The UMR106 cells were cultured as described above until confluence. The cells were then washed twice in phosphate buffered saline followed by incubation for 5 hours at 37° C. in serum free DMEM. After serum deprivation, 100 nM parathyroid hormone (PTH) was added to the cultures and incubation continued for 4, 8, 12, and 16 hours at 37° C. RNA was then isolated from the cells as described above. Northern blot analysis revealed that the PTP-OST message was increased as much as 5 fold upon treatment of the UMR106 cells with 100 nM parathyroid hormone (PTH) for 4 hours with further increases at later time points. Neither of the other two novel PTPase clones were altered by PTH. In addition, serum deprivation and refeeding also did not significantly affect OST-PTP expression. PTH concentrations as low as 1 nM for 18 hours were effective in increasing OST-PTP transcripts but exposure for less than 4 hours regardless of concentration (10 pM–100 nM) had no significant effect. These results demonstrated that OST-PTP was important not only for its exclusionary tissue distribution but also that it functioned in a PTH sensitive manner that indicated a critical role in proper bone metabolism.

Parathyroid hormone modulation of OST-PTP may be mediated through a C-protein coupled pathway utilizing the cyclic AMP-dependent protein kinase (PKA) signalling pathway. Stimulation of osteosarcoma cells using the cyclic AMP analogue, chlorophenylthio-cAMP for 18 hours (10 $\mu$M) resulted in an increase in OST-PTP mRNA levels comparable (5 fold) to that seen with PTH. These results are consistent with the idea that OST-PTP expression is regulated by PTH through stimulation of the PKA signalling pathway which has been demonstrated to modulate expression of other genes involved in osteoblast differentiation (Scott et al., 1992, *Mol. Endo.* 6(12):1834–1842).

EXAMPLE II

Expression and Characterization of Recombinant OST-PTP

The catalytic portion of OST-PTP was expressed as a glutathione-S-transferase fusion protein using the pGEX-KG *E. coli* expression vector. A blunted NotI-XbaI fragment corresponding to the entire cytoplasmic domain of OST-PTP was subcloned into SmaI-XbaI digested pGEX-KG vector. For protein expression, this construct, pKG-OST, was freshly transformed into BL21 strain of *E. coli* and the GST-OST-PTP fusion protein was produced and purified as described previously (Guan et al., 1990, *Proc. Natl. Acad. Sci. USA* 87:1501–1505). The recombinant fusion protein was approximately 70% pure as determined by SDS-PAGE electrophoresis.

Basic kinetic analysis of the recombinant protein was performed using the hydrolysis of the artificial substrate, para-nitrophenylphosphate (pNPP), as the measure of phosphatase activity. Enzyme activity was measured in a 200 $\mu$l reaction comprised of 1) a buffer consisting of 0.1M imidazole, 0.1 mM EDTA, 0.1% β-mercaptoethanol, 2) 20 mM pNPP (saturating conditions), and enzyme. Incubation was carried out at 30° C. for 10 minutes over a range of pH. The reaction was terminated by addition of 800 $\mu$l of 0.25N NaOH. The amount of hydrolyzed product was determined by measurement of absorbance at 410 nm. The extinction coefficient of $1.8 \times 10^4 M^{-1} cm^{-1}$ was used to determine the molar concentration of hydrolyzed pNPP. The maximum activity of OST-PTP incubated with paranitrophenylphosphate (pNPP) at 30° C. for 10 minutes occurred at pH 5.6.

Substrate specificity was determined using tyrosine-phosphorylated Raytide Peptide Substrates (Oncogene Sciences) and serine phosphorylated Kemptide phosphate acceptor peptide (Oncogene Sciences). Raytide Peptide Substrate was phosphorylated on tyrosine by incubating 10 $\mu$g of Raytide Peptide Substrate in a 30 $\mu$l reaction including assay buffer (50 mM Hepes, pH 7.5, 0.1 mM EDTA, 0.1 mg/ml BSA, 10 mM $MgCl_2$, 0.1 mM ATP, 0.2% b-mercaptoethanol), 1.2 $\mu$l $^{32}$P-ATP (6000 Ci/mMol) and 0.5 mg GST-v-src at 30° C. for 30 minutes. Kemptide phosphate acceptor peptide was phosphorylated on serine by incubating 10 $\mu$g of the peptide in a 50 ml reaction including assay buffer (40 mM Tris:HCl, pH 7.5, 10 mM $MgCl_2$, 10 mM dithiothreitol, 0.1 mM ATP), 3 ml $^{32}$P-ATP (6000 Ci/mMol) and 5 $\mu$g of the catalytic subunit of bovine protein kinase A (Fluka) at 30° C. for 30 minutes. The reactions were terminated by addition of 120 $\mu$l of 10% phosphoric acid and applied to P81 filter. Free ATP was removed by 3×100 ml washes with 0.5% phosphoric acid and the peptide eluted with 2×1 ml aliquots of 0.5M ammonium bicarbonate. Aliquots were lyophilized, resuspended in distilled water and radioactivity determined. Phosphatase activity as determined in a 50 $\mu$l reaction containing assay buffer (0.1M imidazole, pH 5.6 or 7.0, 5 mM EDTA, 0.2% b-mercaptoethanol), 100,000 cpms of phosphorylated substrate, and 100 ng–4 $\mu$g of enzyme, incubated at 30° C. for 10 minutes. The reaction was terminated by adding 750 $\mu$l of charcoal mix (0.9M HCl, 90 mM sodium pyrophosphate, 2 mM sodium pyrophosphate dibasic and 4% (vol/vol) Norit. The supernatant was counted to determine the amount of $^{32}$P released. The enzyme rapidly dephosphorylated Raytide Peptide Substrates but not Kemptide phosphate acceptor peptide, demonstrating its specificity to tyrosine residues. These data established that the OST-PTP enzyme dephosphorylated tyrosine residues in proteins with specificity and activity levels typical of previously identified PTPases which control the level of phosphorylation in various cell types.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An isolated nucleic acid comprising the nucleotide sequence shown in SEQ ID NO:1 from nucleotide 205 to 5337.

2. An isolated nucleic acid comprising the nucleotide sequence shown in SEQ ID NO:1 from nucleotide 259 to 5337.

3. An isolated nucleic acid comprising a nucleotide sequence of at least 15 contiguous bases from the sequence shown in SEQ ID NO:1.

4. An isolated nucleic acid comprising a nucleotide sequence which encodes the amino acid sequence from amino acid 19 to amino acid 1711 of SEQ ID NO:2.

5. An isolated nucleic acid which comprises a nucleotide sequence which hybridizes under stringent conditions to the nucleic acid of any one of claims 1 through 4.

6. A vector comprising the nucleic acid of claim 5.

7. A host cell comprising the nucleic acid of claim 5.

8. A vector comprising the nucleic acid of any one of claims 1 to 4.

9. A host cell comprising the nucleic acid of any one of claims 1 to 4.

10. A process for preparing osteoblast-testicular protein tyrosine phosphatase comprising the steps of:

a) transfecting an expression vector comprising a nucleic acid which encodes osteoblast-testicular protein tyrosine phosphatase, which polypeptide comprises the amino acid sequence of SEQ ID NO:2, into a suitable host cell, and b) culturing said host cell under conditions which allow expression of said polypeptide.

11. A process according to claim 10, further comprising the step of isolating said polypeptide.

12. An isolated nucleic acid comprising a nucleotide sequence which encodes the amino acid sequence from amino acid 1 to 1068 of SEQ ID No:2, catalytically functional derivatives and variants thereof having OST-PTP catalytic activity.

13. An isolated nucleic acid comprising a nucleotide sequence which encodes the amino acid sequence from amino acid 18 to amino acid 1068 of SEQ ID No:2, catalytically functional derivatives and variants thereof having OST-PTP catalytic activity.

14. An isolated nucleic acid comprising a nucleotide sequence which encodes the amino acid sequence from amino acid 32 to amino acid 921 of SEQ. ID No. 2, catalytically functional derivatives and variants thereof having OST-PTP catalytic activity.

15. An isolated nucleic acid comprising a nucleotide sequence which encodes the amino acid sequence of SEQ ID No. 2 from amino acid 1348 to amino acid 1359, catalytically functional derivatives and variants thereof having OST-PTP catalytic activity.

16. An isolated nucleic acid comprising a nucleotide sequence which encodes the amino acid sequence of SEQ ID No. 2 from amino acid 1668 to amino acid 1678, catalytically functional derivatives and variants thereof having OST-PTP catalytic activity.

17. An isolated nucleic acid comprising a nucleotide sequence which encodes the amino acid sequence of SEQ ID No. 2 from amino acid 1348 to amino acid 1359 and wherein the cysteine at position 1350 is replaced by serine.

18. An isolated nucleic acid comprising a nucleotide sequence which encodes the amino acid sequence from amino acid 32 to 1678 of SEQ ID No. 2, catalytically functional derivatives and variants thereof having OST-PTP catalytic activity.

19. An isolated nucleic acid comprising a nucleotide sequence which encodes the amino acid sequence from amino acid 1 to 1104 of SEQ ID No. 2, catalytically functional derivatives and variants thereof having OST-PTP catalytic activity.

20. An isolated nucleic acid comprising a nucleotide sequence which encodes the amino acid sequence from amino acid 1105 to 1171 of SEQ ID No. 2, catalytically functional derivatives and variants thereof having OST-PTP catalytic activity.

21. An isolated nucleic acid comprising a nucleotide sequence which encodes the amino acid sequence of SEQ ID No. 2 from amino acid 1348 to amidino acid 1678, catalytically functional derivatives and variants thereof having OST-PTP catalytic activity.

22. An isolated nucleic acid which comprises a nucleotide sequence which hybridizes under stringent conditions to a nucleic acid of any of claims 12 to 21.

23. A vector comprising the nucleic acid of any of claims 12 to 21.

24. A vector comprising the nucleic acid of claim 22.

25. A host cell comprising the nucleic acid of any of claims 12 to 21.

26. A host cell comprising the nucleic acid of claim 22.

27. A process for preparing a polypeptide comprising:

a) transfecting an expression vector comprising the nucleic acid of any of claims 12 to 21 and which encodes the polypeptide into a suitable host cell; and b) culturing said host cell under conditions which allow expression of the polypeptide.

28. A process for preparing a polypeptide having OST-PTP tyrosine phosphatase activity comprising:

a) transfecting an expression vector comprising the isolated nucleic acid of claim 22 that encodes the polypeptide having the OST-PTP tyrosine phosphatase activity into a suitable host cell; and b) culturing said host cell under conditions which allow expression of the polypeptide.

29. A process according to claim 27, further comprising the step of isolating the polypeptide.

30. A process according to claim 28, further comprising the step of isolating the polypeptide.

* * * * *

UNITED STATES PATENT AND TRADEMARK OFFICE
CERTIFICATE OF CORRECTION

PATENT NO. : 5,821,084

DATED : October 13, 1998

INVENTOR(S) : Olmsted et al

It is certified that error appears in the above-identified patent and that said Letters Patent is hereby corrected as shown below:

On the title page: Item [56]

column 1, "Other Publications", the third Charbonneau et al. reference, "the" should be --The--; The last reference, Genovese et al., "swquences" should be --sequences--.

column 2, second Guan et al. reference, "protein-tyroisne-phosphatase" should be --protein-tyrosine-phosphatase--; First Hunter reference, "All tail" should be --A tail--; Kerszenbaur reference, "in virto" should be --in vitro--; and "endocrine Rev." should be --Endocrine Rev.--; Matthews reference, "phosphatases" should be --phosphatase--.

column 1, Ralph et al. reference, "huaman" should be --human--.

Column 3, line 4, "osteoblast" should be --Osteoblast--;
line 36, "ohahi" should be --Ohahi--.

UNITED STATES PATENT AND TRADEMARK OFFICE
CERTIFICATE OF CORRECTION

PATENT NO. : 5,821,084
DATED : October 13, 1998
INVENTOR(S) : OLMSTED et al.

It is certified that error appears in the above-identified patent and that said Letters Patent is hereby corrected as shown below:

Column 6, line 63, "G." should be --G,-- and "H." should be --H,--.

Column 10, line 56, "or" should be --the--.

Column 15, line 42, "(mAhs)" should be --(mAbs)--;
  line 55, "mAh" should be --mAb--.

Column 19, line 55, delete "is".

Column 21, line 36, "C-protein" should be --G-protein--.

Signed and Sealed this

Twenty-seventh Day of April, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 5455 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 205..5337

( x i ) SEQUENCE DESCRIPTION: SEQ ID NO:1:

```
AGAACAGCCT  ACAACAGCTG  CCTTCCGGGA  GGGACCAGGC  TAGTTCACAC  TTGGAAGTTG        60

GGATGCCAGG  AGCAGCCTTC  TGTCTTCCGA  GGCCTTCCTG  GGTCTCCTGG  TCAGCTCATT       120

CCACACTGAG  ATGATTCTAA  AGAAAGATCC  TCACACAGAC  TCTGCTGGAA  GAAACAAAGT       180

GAAGTGTCCC  CAGACTTTAT  CAGG ATG AGG CCC CTG ATT CTG TTA GCT GCC             231
                            Met Arg Pro Leu Ile Leu Leu Ala Ala
                              1               5

CTC CTC TGG CTC CAG GGC TTT TTG GCC GAG GAC GAC GCA TGC TCA TCC              279
Leu Leu Trp Leu Gln Gly Phe Leu Ala Glu Asp Asp Ala Cys Ser Ser
 10              15                  20                  25

TTG GAA GGG AGC CCA GAC AGG CAG GGT GGA GGT CCA CTT CTG AGT GTG              327
Leu Glu Gly Ser Pro Asp Arg Gln Gly Gly Gly Pro Leu Leu Ser Val
             30                  35                  40

AAC GTC AGT AGC CAT GGA AAG TCT ACC AGC CTG TTT CTG AGC TGG GTA              375
Asn Val Ser Ser His Gly Lys Ser Thr Ser Leu Phe Leu Ser Trp Val
             45                  50                  55

GCT GCA GAG CTG GGC GGA TTT GAC TAT GCC CTC AGC CTC AGG AGT GTG              423
Ala Ala Glu Leu Gly Gly Phe Asp Tyr Ala Leu Ser Leu Arg Ser Val
             60                  65                  70

AAC TCC TCA GGT TCT CCA GAA GGG CAA CAG CTC CAG GCT CAC ACA AAT              471
Asn Ser Ser Gly Ser Pro Glu Gly Gln Gln Leu Gln Ala His Thr Asn
 75                  80                  85

GAG TCC GGC TTT GAG TTC CAT GGC CTG GTG CCA GGG AGT CGC TAC CAG              519
Glu Ser Gly Phe Glu Phe His Gly Leu Val Pro Gly Ser Arg Tyr Gln
 90                  95                 100                 105

CTA AAA CTG ACT GTC CTA AGA CCC TGT TGG CAG AAT GTC ACA ATT ACC              567
Leu Lys Leu Thr Val Leu Arg Pro Cys Trp Gln Asn Val Thr Ile Thr
             110                 115                 120

CTC ACT GCC CGA ACT GCC CCG ACA GTG GTC CGT GGA CTG CAG CTG CAT              615
Leu Thr Ala Arg Thr Ala Pro Thr Val Val Arg Gly Leu Gln Leu His
             125                 130                 135

AGC GCT GGG AGC CCA GCC AGG CTG GAA GCC TCG TGG AGT GAT GCC CCT              663
Ser Ala Gly Ser Pro Ala Arg Leu Glu Ala Ser Trp Ser Asp Ala Pro
             140                 145                 150

GGA GAT CAA GAC AGC TAC CAA CTT CTC CTC TAC CAC CTG GAA TCC CAA              711
Gly Asp Gln Asp Ser Tyr Gln Leu Leu Leu Tyr His Leu Glu Ser Gln
 155                 160                 165

ACT CTG GCA TGC AAT GTC TCT GTG TCC CCT GAC ACC CTG TCT TAC AGT              759
Thr Leu Ala Cys Asn Val Ser Val Ser Pro Asp Thr Leu Ser Tyr Ser
170                  175                 180                 185

TTT GGC GAC CTT TTG CCA GGT ACT CAG TAT GTC TTG GAG GTT ATC ACC              807
Phe Gly Asp Leu Leu Pro Gly Thr Gln Tyr Val Leu Glu Val Ile Thr
             190                 195                 200
```

| | | | | | | | | | | | | | | | | |
|---|---|---|---|---|---|---|---|---|---|---|---|---|---|---|---|---|
| TGG | GCT | GGC | AGT | CTC | CAT | GCG | AAG | ACT | AGT | ATC | CTC | CAG | TGG | ACA | GAG | 855 |
| Trp | Ala | Gly | Ser 205 | Leu | His | Ala | Lys 210 | Thr | Ser | Ile | Leu | Gln 215 | Trp | Thr | Glu | |
| CCT | GTC | CCT | CCT | GAT | CAC | CTA | GCA | CTA | CGT | GCC | TTG | GGT | ACC | AGT | AGC | 903 |
| Pro | Val | Pro 220 | Pro | Asp | His | Leu | Ala 225 | Leu | Arg | Ala | Leu | Gly 230 | Thr | Ser | Ser | |
| CTG | CAA | GCC | TTC | TGG | AAC | AGC | TCT | GAA | GGG | GCC | ACC | TCG | TTT | CAC | CTG | 951 |
| Leu | Gln 235 | Ala | Phe | Trp | Asn | Ser 240 | Ser | Glu | Gly | Ala | Thr 245 | Ser | Phe | His | Leu | |
| ATG | CTC | ACA | GAC | CTC | CTC | GGG | GGC | ACC | AAC | ACG | ACT | GCG | GTG | ATC | AGA | 999 |
| Met | Leu 250 | Thr | Asp | Leu | Leu 255 | Gly | Gly | Thr | Asn | Thr 260 | Thr | Ala | Val | Ile | Arg 265 | |
| CAA | GGG | GTC | TCG | ACC | CAC | ACC | TTT | CTT | CAC | CTA | TCT | CCG | GGT | ACA | CCT | 1047 |
| Gln | Gly | Val | Ser | Thr 270 | His | Thr | Phe | Leu | His 275 | Leu | Ser | Pro | Gly | Thr 280 | Pro | |
| CAT | GAG | CTG | AAG | ATT | TGT | GCT | TCT | GCT | GGG | CCC | CAC | CAG | ATC | TGG | GGA | 1095 |
| His | Glu | Leu | Lys 285 | Ile | Cys | Ala | Ser | Ala 290 | Gly | Pro | His | Gln | Ile 295 | Trp | Gly | |
| CCC | AGT | GCC | ACC | GAG | TGG | ACC | TAT | CCC | TCT | TAC | CCA | TCT | GAC | CTG | GTG | 1143 |
| Pro | Ser | Ala 300 | Thr | Glu | Trp | Thr | Tyr 305 | Pro | Ser | Tyr | Pro | Ser 310 | Asp | Leu | Val | |
| CTG | ACT | CCC | TTA | CGG | AAT | GAG | CTC | TGG | GCC | AGC | TGG | AAG | GCA | GGG | CTG | 1191 |
| Leu | Thr 315 | Pro | Leu | Arg | Asn | Glu 320 | Leu | Trp | Ala | Ser | Trp 325 | Lys | Ala | Gly | Leu | |
| GGA | GCC | CGG | GAC | GGC | TAT | GTA | CTG | AAG | TTA | AGT | GGG | CCA | ATG | GAG | AGT | 1239 |
| Gly 330 | Ala | Arg | Asp | Gly | Tyr 335 | Val | Leu | Lys | Leu | Ser 340 | Gly | Pro | Met | Glu | Ser 345 | |
| ACG | TCT | ACC | CTG | GGC | CCG | GAA | GAG | TGC | AAT | GCA | GTC | TTC | CCA | GGG | CCC | 1287 |
| Thr | Ser | Thr | Leu | Gly 350 | Pro | Glu | Glu | Cys | Asn 355 | Ala | Val | Phe | Pro | Gly 360 | Pro | |
| CTG | CCT | CCG | GGA | CAC | TAC | ACT | TTG | CAG | CTG | AAG | GTT | CTA | GCT | GGA | CCT | 1335 |
| Leu | Pro | Pro | Gly | His 365 | Tyr | Thr | Leu | Gln | Leu 370 | Lys | Val | Leu | Ala | Gly 375 | Pro | |
| TAT | GAT | GCC | TGG | GTG | GAG | GGC | AGT | ACC | TGG | CTG | GCT | GAA | TCT | GCT | GCC | 1383 |
| Tyr | Asp | Ala 380 | Trp | Val | Glu | Gly | Ser 385 | Thr | Trp | Leu | Ala | Glu 390 | Ser | Ala | Ala | |
| CTT | CCC | AGG | GAG | GTC | CCT | GGT | GCC | AGA | CTG | TGG | CTA | GAT | GGA | CTG | GAA | 1431 |
| Leu | Pro 395 | Arg | Glu | Val | Pro | Gly 400 | Ala | Arg | Leu | Trp | Leu 405 | Asp | Gly | Leu | Glu | |
| GCT | TCC | AAG | CAG | CCT | GGG | AGA | CGG | GCG | CTA | CTC | TAT | TCT | GAC | GAT | GCC | 1479 |
| Ala | Ser | Lys | Gln 410 | Pro | Gly | Arg | Arg | Ala 415 | Leu | Leu | Tyr | Ser | Asp 420 | Asp | Ala 425 | |
| CCA | GGC | TCC | CTA | GGG | AAC | ATC | TCT | GTG | CCC | TCT | GGT | GCC | ACT | CAC | GTC | 1527 |
| Pro | Gly | Ser | Leu | Gly 430 | Asn | Ile | Ser | Val | Pro 435 | Ser | Gly | Ala | Thr | His 440 | Val | |
| ATT | TTC | TGT | GGC | CTG | GTA | CCT | GGA | GCC | CAC | TAT | AGG | GTG | GAC | ATT | GCC | 1575 |
| Ile | Phe | Cys | Gly 445 | Leu | Val | Pro | Gly | Ala 450 | His | Tyr | Arg | Val | Asp 455 | Ile | Ala | |
| TCA | TCC | ACG | GGG | GAC | ATC | TCT | CAG | AGC | ATC | TCA | GGC | TAT | ACA | AGT | CCC | 1623 |
| Ser | Ser | Thr | Gly 460 | Asp | Ile | Ser | Gln | Ser 465 | Ile | Ser | Gly | Tyr | Thr 470 | Ser | Pro | |
| CTG | CCA | CCG | CAG | TCA | CTG | GAG | GTC | ATC | AGC | AGG | AGC | AGC | CCA | TCT | GAC | 1671 |
| Leu | Pro | Pro | Gln | Ser 475 | Leu | Glu | Val | Ile | Ser 480 | Arg | Ser | Ser | Pro | Ser 485 | Asp | |
| CTG | ACT | ATT | GCT | TGG | GGT | CCA | GCA | CCA | GGG | CAG | CTG | GAA | GGT | TAT | AAG | 1719 |
| Leu | Thr | Ile | Ala | Trp 490 | Gly | Pro | Ala | Pro | Gly 495 | Gln | Leu | Glu | Gly | Tyr 500 | Lys 505 | |
| GTT | ACC | TGG | CAT | CAG | GAT | GGC | AGC | CAG | AGG | TCT | CCT | GGC | GAC | CTT | GTT | 1767 |
| Val | Thr | Trp | His | Gln 510 | Asp | Gly | Ser | Gln | Arg 515 | Ser | Pro | Gly | Asp | Leu 520 | Val | |

-continued

| | | | | | | | | | | | | | | | | |
|---|---|---|---|---|---|---|---|---|---|---|---|---|---|---|---|---|
| GAC | TTG | GGC | CCT | GAC | ACT | TTG | AGC | CTG | ACT | CTG | AAA | TCT | CTG | GTA | CCC | 1815 |
| Asp | Leu | Gly | Pro 525 | Asp | Thr | Leu | Ser | Leu 530 | Thr | Leu | Lys | Ser | Leu 535 | Val | Pro | |
| GGC | TCC | TGC | TAC | ACC | GTG | TCA | GCA | TGG | GCC | TGG | GCC | GGG | AAC | CTC | AGC | 1863 |
| Gly | Ser | Cys 540 | Tyr | Thr | Val | Ser | Ala 545 | Trp | Ala | Trp | Ala | Gly 550 | Asn | Leu | Ser | |
| TCT | GAC | TCT | CAG | AAG | ATT | CAC | AGC | TGC | ACC | CGC | CCC | GCT | CCT | CCC | ACC | 1911 |
| Ser | Asp 555 | Ser | Gln | Lys | Ile | His 560 | Ser | Cys | Thr | Arg | Pro 565 | Ala | Pro | Pro | Thr | |
| AAC | CTG | AGT | CTG | GGC | TTT | GCC | CAC | CAG | CCT | GCG | GCA | CTG | AAG | GCT | TCC | 1959 |
| Asn 570 | Leu | Ser | Leu | Gly | Phe 575 | Ala | His | Gln | Pro | Ala 580 | Ala | Leu | Lys | Ala | Ser 585 | |
| TGG | TAT | CAC | CCA | CCG | GGT | GGC | AGG | GAT | GCC | TTT | CAC | TTA | CGG | CTT | TAC | 2007 |
| Trp | Tyr | His | Pro | Pro 590 | Gly | Gly | Arg | Asp | Ala 595 | Phe | His | Leu | Arg | Leu 600 | Tyr | |
| AGG | CTG | AGG | CCT | CTG | ACA | CTG | GAA | AGT | GAG | AAG | GTC | CTA | CCT | CGG | GAG | 2055 |
| Arg | Leu | Arg | Pro 605 | Leu | Thr | Leu | Glu | Ser 610 | Glu | Lys | Val | Leu | Pro 615 | Arg | Glu | |
| GCC | CAG | AAC | TTC | TCC | TGG | GCC | CAG | CTG | ACT | GCA | GGC | TGT | GAG | TTC | CAG | 2103 |
| Ala | Gln | Asn 620 | Phe | Ser | Trp | Ala | Gln 625 | Leu | Thr | Ala | Gly | Cys 630 | Glu | Phe | Gln | |
| GTA | CAG | CTG | TCT | ACC | TTG | TGG | GGG | TCT | GAG | AGA | AGC | AGC | AGT | GCC | AAC | 2151 |
| Val | Gln 635 | Leu | Ser | Thr | Leu | Trp 640 | Gly | Ser | Glu | Arg | Ser 645 | Ser | Ser | Ala | Asn | |
| GCC | ACA | GGC | TGG | ACA | CCC | CCT | TCA | GCT | CCT | ACA | CTG | GTA | AAC | GTG | ACC | 2199 |
| Ala 650 | Thr | Gly | Trp | Thr | Pro 655 | Pro | Ser | Ala | Pro | Thr 660 | Leu | Val | Asn | Val | Thr 665 | |
| AGC | GAT | GCT | CCT | ACC | CAG | CTC | CAA | GTA | TCC | TGG | GCC | CAC | GTT | CCT | GGG | 2247 |
| Ser | Asp | Ala | Pro | Thr 670 | Gln | Leu | Gln | Val | Ser 675 | Trp | Ala | His | Val | Pro 680 | Gly | |
| GGC | CGG | AGC | CGC | TAC | CAA | GTG | ACC | CTA | TAC | CAG | GAG | AGT | ACC | CGG | ACA | 2295 |
| Gly | Arg | Ser | Arg 685 | Tyr | Gln | Val | Thr | Leu 690 | Tyr | Gln | Glu | Ser | Thr 695 | Arg | Thr | |
| GCC | ACC | AGC | ATC | ATG | GGG | CCC | AAG | GAA | GAT | GGC | ACG | AGC | TTT | TTG | GGT | 2343 |
| Ala | Thr | Ser 700 | Ile | Met | Gly | Pro | Lys 705 | Glu | Asp | Gly | Thr | Ser 710 | Phe | Leu | Gly | |
| TTG | ACT | CCT | GGC | ACT | AAG | TAC | AAG | GTG | GAA | GTC | ATC | TCC | TGG | GCT | GGG | 2391 |
| Leu | Thr 715 | Pro | Gly | Thr | Lys | Tyr 720 | Lys | Val | Glu | Val | Ile 725 | Ser | Trp | Ala | Gly | |
| CCC | CTC | TAC | ACT | GCA | GCA | GCC | AAC | GTT | TCT | GCC | TGG | ACC | TAC | CCA | CTC | 2439 |
| Pro 730 | Leu | Tyr | Thr | Ala | Ala 735 | Ala | Asn | Val | Ser | Ala 740 | Trp | Thr | Tyr | Pro | Leu 745 | |
| ATA | CCC | AAT | GAG | CTG | CTC | GTG | TCA | ATG | CAG | GCA | GGC | AGT | GCT | GTG | GTT | 2487 |
| Ile | Pro | Asn | Glu | Leu 750 | Leu | Val | Ser | Met | Gln 755 | Ala | Gly | Ser | Ala | Val 760 | Val | |
| AAC | CTG | GCC | TGG | CCC | AGT | GGT | CCC | CTG | GGG | CAA | GGG | GCA | TGC | CAC | GCC | 2535 |
| Asn | Leu | Ala | Trp 765 | Pro | Ser | Gly | Pro | Leu 770 | Gly | Gln | Gly | Ala | Cys 775 | His | Ala | |
| CAA | CTC | TCA | GAT | GCT | GGA | CAC | CTC | TCA | TGG | GAG | CAA | CCC | CTG | AAA | CTA | 2583 |
| Gln | Leu | Ser 780 | Asp | Ala | Gly | His | Leu 785 | Ser | Trp | Glu | Gln | Pro 790 | Leu | Lys | Leu | |
| GGC | CAA | GAG | CTC | TTC | ATG | CTA | AGG | GAT | CTC | ACA | CCA | GGA | CAT | ACC | ATC | 2631 |
| Gly | Gln | Glu 795 | Leu | Phe | Met | Leu | Arg 800 | Asp | Leu | Thr | Pro | Gly 805 | His | Thr | Ile | |
| TCG | ATG | TCA | GTG | AGG | TGT | CGG | GCA | GGG | CCG | CTC | CAG | GCC | TCT | ACG | CAC | 2679 |
| Ser | Met | Ser | Val | Arg 815 | Cys | Arg | Ala | Gly | Pro 820 | Leu | Gln | Ala | Ser | Thr 825 | His | |
| | | | 810 | | | | | | | | | | | | | |
| CTT | GTG | GTG | CTG | TCT | GTG | GAG | CCT | GGC | CCT | GTG | GAA | GAT | GTG | CTC | TGT | 2727 |
| Leu | Val | Val | Leu | Ser 830 | Val | Glu | Pro | Gly | Pro 835 | Val | Glu | Asp | Val | Leu 840 | Cys | |

```
CAT CCA GAG GCC ACC TAC CTG GCC CTG AAC TGG ACG ATG CCT GCT GGA          2775
His Pro Glu Ala Thr Tyr Leu Ala Leu Asn Trp Thr Met Pro Ala Gly
            845                 850                 855

GAC GTG GAT GTC TGT CTG GTG GTG GTA GAG CGG CTG GTG CCG GGA GGG          2823
Asp Val Asp Val Cys Leu Val Val Val Glu Arg Leu Val Pro Gly Gly
            860                 865                 870

GGC ACT CAT TTT GTC TTC CAG GTC AAC ACC TCA GGG GAT GCT CTT CTG          2871
Gly Thr His Phe Val Phe Gln Val Asn Thr Ser Gly Asp Ala Leu Leu
            875                 880                 885

TTG CCC AAC TTG ATG CCC ACC ACT TCT TAC CGC CTT AGC CTC ACC GTT          2919
Leu Pro Asn Leu Met Pro Thr Thr Ser Tyr Arg Leu Ser Leu Thr Val
890                 895                 900                 905

CTG GGC AGG AAT AGT CGG TGG AGC CGG GCG GTT TCC CTG GTG TGC AGT          2967
Leu Gly Arg Asn Ser Arg Trp Ser Arg Ala Val Ser Leu Val Cys Ser
                910                 915                 920

ACT TCT GCT GAG GCT TGG CAC CCC CCA GAG CTA GCT GAG CCC CCC CAG          3015
Thr Ser Ala Glu Ala Trp His Pro Pro Glu Leu Ala Glu Pro Pro Gln
            925                 930                 935

GTG GAG CTG GGG ACA GGG ATG GGT GTG ACA GTC ATG CGT GGC ATG TTT          3063
Val Glu Leu Gly Thr Gly Met Gly Val Thr Val Met Arg Gly Met Phe
            940                 945                 950

GGT AAA GAT GAC GGG CAG ATC CAG TGG TAT GGC ATA ATT GCC ACC ATC          3111
Gly Lys Asp Asp Gly Gln Ile Gln Trp Tyr Gly Ile Ile Ala Thr Ile
            955                 960                 965

AAC ATG ACG CTG GCC CAG CCT TCC CGG GAA GCC ATC AAT TAC ACA TGG          3159
Asn Met Thr Leu Ala Gln Pro Ser Arg Glu Ala Ile Asn Tyr Thr Trp
970                 975                 980                 985

TAT GAC CAC TAC TAT AGA GGA TGT GAG TCC TTC CTG GCT CTC CTG TTC          3207
Tyr Asp His Tyr Tyr Arg Gly Cys Glu Ser Phe Leu Ala Leu Leu Phe
                990                 995                 1000

CCA AAC CCC TTC TAC CCA GAG CCT TGG GCT GGG CCA AGA TCC TGG ACA          3255
Pro Asn Pro Phe Tyr Pro Glu Pro Trp Ala Gly Pro Arg Ser Trp Thr
            1005                1010                1015

GTA CCT GTG GGT ACT GAG GAC TGT GAC AAC ACC CAA GAG ATA TGC AAT          3303
Val Pro Val Gly Thr Glu Asp Cys Asp Asn Thr Gln Glu Ile Cys Asn
            1020                1025                1030

GGG CGT CTC AAG TCA GGC TTC CAG TAT AGG TTC AGC GTT GTG GCC TTT          3351
Gly Arg Leu Lys Ser Gly Phe Gln Tyr Arg Phe Ser Val Val Ala Phe
            1035                1040                1045

AGT AGG CTC AAC ACT CCA GAG ACC ATC CTC GCC TTC TCG GCC TTC TCA          3399
Ser Arg Leu Asn Thr Pro Glu Thr Ile Leu Ala Phe Ser Ala Phe Ser
1050                1055                1060                1065

GAG CCC CGG GCC AGC ATC TCT CTG GCG ATC ATT CCC CTG ACA GTT ATG          3447
Glu Pro Arg Ala Ser Ile Ser Leu Ala Ile Ile Pro Leu Thr Val Met
                1070                1075                1080

CTG GGG GCT GTG GTG GGC AGC ATT GTC ATT GTG TGT GCA GTG CTA TGC          3495
Leu Gly Ala Val Val Gly Ser Ile Val Ile Val Cys Ala Val Leu Cys
            1085                1090                1095

TTG CTC CGC TGG CGG TGC CTG AAG GGA CCA AGA TCA GAG AAG GAT GGC          3543
Leu Leu Arg Trp Arg Cys Leu Lys Gly Pro Arg Ser Glu Lys Asp Gly
            1100                1105                1110

TTT TCC AAG GAG CTG ATG CCT TAC AAC CTG TGG CGG ACC CAT CGG CCT          3591
Phe Ser Lys Glu Leu Met Pro Tyr Asn Leu Trp Arg Thr His Arg Pro
            1115                1120                1125

ATC CCC ATC CAT AGC TTC CGG CAG AGC TAT GAG GCC AAG AGC GCA CAT          3639
Ile Pro Ile His Ser Phe Arg Gln Ser Tyr Glu Ala Lys Ser Ala His
1130                1135                1140                1145

GCA CAC CAG ACC TTC TTC CAG GAA TTT GAG GAG TTG AAG GAG GTA GGC          3687
Ala His Gln Thr Phe Phe Gln Glu Phe Glu Glu Leu Lys Glu Val Gly
                1150                1155                1160
```

```
AAG GAC CAG CCC CGA CTA GAG GCT GAG CAT CCG GAC AAC ATC ATC AAG        3735
Lys Asp Gln Pro Arg Leu Glu Ala Glu His Pro Asp Asn Ile Ile Lys
            1165                1170                1175

AAC CGG TAC CCA CAC GTG CTG CCC TAT GAC CAC TCC AGG GTC AGG CTG        3783
Asn Arg Tyr Pro His Val Leu Pro Tyr Asp His Ser Arg Val Arg Leu
            1180                1185                1190

ACC CAG CTA CCA GGA GAG CCT CAT TCT GAC TAC ATC AAT GCC AAC TTC        3831
Thr Gln Leu Pro Gly Glu Pro His Ser Asp Tyr Ile Asn Ala Asn Phe
    1195                1200                1205

ATC CCA GGC TAT AGC CAC ACA CAG GAG ATC ATT GCC ACC CAG GGG CCT        3879
Ile Pro Gly Tyr Ser His Thr Gln Glu Ile Ile Ala Thr Gln Gly Pro
1210            1215                1220                1225

CTC AAA AAG ACG CTA GAG GAC TTC TGG CGG TTG GTA TGG GAG CAG CAA        3927
Leu Lys Lys Thr Leu Glu Asp Phe Trp Arg Leu Val Trp Glu Gln Gln
                1230                1235                1240

GTC CAC GTG ATC ATC ATG CTG ACT GTG GGC ATG GAG AAC GGG CGG GTA        3975
Val His Val Ile Ile Met Leu Thr Val Gly Met Glu Asn Gly Arg Val
                1245                1250                1255

CTG TGT GAG CAC TAC TGG CCA GCC AAC TCC ACG CCT GTT ACT CAC GGT        4023
Leu Cys Glu His Tyr Trp Pro Ala Asn Ser Thr Pro Val Thr His Gly
                1260                1265                1270

CAC ATC ACC ATC CAC CTC CTG GCA GAG GAG CCT GAG GAT GAG TGG ACC        4071
His Ile Thr Ile His Leu Leu Ala Glu Glu Pro Glu Asp Glu Trp Thr
            1275                1280                1285

AGG AGG GAA TTC CAG CTG CAG CAC GGT ACC GAG CAA AAA CAG AGG CGA        4119
Arg Arg Glu Phe Gln Leu Gln His Gly Thr Glu Gln Lys Gln Arg Arg
1290                1295                1300                1305

GTG AAG CAG CTG CAG TTC ACT ACC TGG CCA GAC CAC AGT GTC CCG GAG        4167
Val Lys Gln Leu Gln Phe Thr Thr Trp Pro Asp His Ser Val Pro Glu
                1310                1315                1320

GCT CCC AGC TCT CTG CTC GCT TTT GTA GAA CTG GTA CAG GAG CAG GTG        4215
Ala Pro Ser Ser Leu Leu Ala Phe Val Glu Leu Val Gln Glu Gln Val
            1325                1330                1335

CAG GCC ACT CAG GGC AAG GGA CCC ATC CTG GTG CAT TGC AGT GCT GGC        4263
Gln Ala Thr Gln Gly Lys Gly Pro Ile Leu Val His Cys Ser Ala Gly
            1340                1345                1350

GTG GGG AGG ACA GGC ACC TTT GTG GCT CTC TTG CGG CTA CTG CGA CAA        4311
Val Gly Arg Thr Gly Thr Phe Val Ala Leu Leu Arg Leu Leu Arg Gln
    1355                1360                1365

CTA GAG GAA GAG AAG GTG GCC GAT GTG TTC AAC ACT GTG TAC ATA CTC        4359
Leu Glu Glu Glu Lys Val Ala Asp Val Phe Asn Thr Val Tyr Ile Leu
1370                1375                1380                1385

CGG TTG CAC CGG CCC CTC ATG ATC CAG ACC CTG AGT CAA TAC ATC TTC        4407
Arg Leu His Arg Pro Leu Met Ile Gln Thr Leu Ser Gln Tyr Ile Phe
            1390                1395                1400

CTG CAC AGT TGC CTG CTG AAC AAG ATT CTG GAA GGG CCC CCT GAC AGC        4455
Leu His Ser Cys Leu Leu Asn Lys Ile Leu Glu Gly Pro Pro Asp Ser
            1405                1410                1415

TCC GAC TCC GGC CCC ATC TCT GTG ATG GAT TTT GCA CAG GCT TGT GCC        4503
Ser Asp Ser Gly Pro Ile Ser Val Met Asp Phe Ala Gln Ala Cys Ala
            1420                1425                1430

AAG AGG GCA GCC AAC GCC AAT GCT GGT TTC TTG AAG GAG TAC AAG CTC        4551
Lys Arg Ala Ala Asn Ala Asn Ala Gly Phe Leu Lys Glu Tyr Lys Leu
            1435                1440                1445

CTG AAG CAG GCC ATC AAG GAT GGG ACT GGC TCT CTG CTG CCC CCT CCT        4599
Leu Lys Gln Ala Ile Lys Asp Gly Thr Gly Ser Leu Leu Pro Pro Pro
1450                1455                1460                1465

GAC TAC AAT CAG AAC AGC ATT GTC TCC CGT CGT CAT TCT CAG GAG CAG        4647
Asp Tyr Asn Gln Asn Ser Ile Val Ser Arg Arg His Ser Gln Glu Gln
                1470                1475                1480
```

| | | | | | | | | | | | | | | | | |
|---|---|---|---|---|---|---|---|---|---|---|---|---|---|---|---|---|
| TTC | GCC | CTG | GTG | GAG | GAG | TGC | CCT | GAG | GAT | AGC | ATG | CTG | GAA | GCC | TCA | 4695 |
| Phe | Ala | Leu | Val | Glu | Glu | Cys | Pro | Glu | Asp | Ser | Met | Leu | Glu | Ala | Ser | |
| | | | 1485 | | | | 1490 | | | | | 1495 | | | | |
| CTC | TTC | CCT | GGT | GGT | CCG | TCT | GGT | TGT | GAT | CAT | GTG | GTG | CTG | ACT | GGC | 4743 |
| Leu | Phe | Pro | Gly | Gly | Pro | Ser | Gly | Cys | Asp | His | Val | Val | Leu | Thr | Gly | |
| | | 1500 | | | | | 1505 | | | | | 1510 | | | | |
| TCA | GCC | GGA | CCA | AAG | GAA | CTC | TGG | GAA | ATG | GTG | TGG | GAG | CAT | GAT | GCC | 4791 |
| Ser | Ala | Gly | Pro | Lys | Glu | Leu | Trp | Glu | Met | Val | Trp | Glu | His | Asp | Ala | |
| | | 1515 | | | | | 1520 | | | | | 1525 | | | | |
| CAT | GTG | CTC | GTC | TCC | CTG | GGC | CTG | CCT | GAT | ACC | AAG | GAG | AAG | CCA | CCA | 4839 |
| His | Val | Leu | Val | Ser | Leu | Gly | Leu | Pro | Asp | Thr | Lys | Glu | Lys | Pro | Pro | |
| 1530 | | | | | 1535 | | | | | 1540 | | | | | 1545 | |
| GAC | ATC | TGG | CCA | GTG | GAG | ATG | CAG | CCT | ATT | GTC | ACA | GAC | ATG | GTG | ACA | 4887 |
| Asp | Ile | Trp | Pro | Val | Glu | Met | Gln | Pro | Ile | Val | Thr | Asp | Met | Val | Thr | |
| | | | | 1550 | | | | | 1555 | | | | | 1560 | | |
| GTG | CAC | AGA | GTG | TCT | GAG | AGC | AAC | ACA | ACA | ACT | GGC | TGG | CCC | AGC | ACC | 4935 |
| Val | His | Arg | Val | Ser | Glu | Ser | Asn | Thr | Thr | Thr | Gly | Trp | Pro | Ser | Thr | |
| | | | | 1565 | | | | | 1570 | | | | | 1575 | | |
| CTC | TTC | AGA | GTC | ATA | CAC | GGG | GAG | AGT | GGA | AAG | GAA | AGG | CAG | GTT | CAA | 4983 |
| Leu | Phe | Arg | Val | Ile | His | Gly | Glu | Ser | Gly | Lys | Glu | Arg | Gln | Val | Gln | |
| | | | 1580 | | | | | 1585 | | | | | 1590 | | | |
| TGC | CTG | CAA | TTT | CCA | TGC | TCT | GAG | TCT | GGG | TGT | GAG | CTC | CCA | GCT | AAC | 5031 |
| Cys | Leu | Gln | Phe | Pro | Cys | Ser | Glu | Ser | Gly | Cys | Glu | Leu | Pro | Ala | Asn | |
| | | 1595 | | | | | 1600 | | | | | 1605 | | | | |
| ACC | CTA | CTG | ACC | TTC | CTT | GAT | GCT | GTG | GGC | CAG | TGC | TGC | TTC | CGG | GGC | 5079 |
| Thr | Leu | Leu | Thr | Phe | Leu | Asp | Ala | Val | Gly | Gln | Cys | Cys | Phe | Arg | Gly | |
| 1610 | | | | | 1615 | | | | | 1620 | | | | | 1625 | |
| AAG | AGC | AAG | AAG | CCA | GGG | ACC | CTG | CTC | AGC | CAC | TCC | AGC | AAA | AAC | ACA | 5127 |
| Lys | Ser | Lys | Lys | Pro | Gly | Thr | Leu | Leu | Ser | His | Ser | Ser | Lys | Asn | Thr | |
| | | | | 1630 | | | | | 1635 | | | | | 1640 | | |
| AAC | CAG | CTG | GGC | ACC | TTC | TTG | GCT | ATG | GAA | CAG | CTG | TTA | CAG | CAA | GCA | 5175 |
| Asn | Gln | Leu | Gly | Thr | Phe | Leu | Ala | Met | Glu | Gln | Leu | Leu | Gln | Gln | Ala | |
| | | | 1645 | | | | | 1650 | | | | | 1655 | | | |
| GGG | ACA | GAG | CGC | ACA | GTG | GAC | GTC | TTC | AAT | GTG | GCC | CTG | AAG | CAG | TCA | 5223 |
| Gly | Thr | Glu | Arg | Thr | Val | Asp | Val | Phe | Asn | Val | Ala | Leu | Lys | Gln | Ser | |
| | | | 1660 | | | | | 1665 | | | | | 1670 | | | |
| CAG | GCC | TGC | GGC | CTT | ATG | ACC | CCA | ACA | CTG | GAG | CAG | TAT | ATC | TAC | CTC | 5271 |
| Gln | Ala | Cys | Gly | Leu | Met | Thr | Pro | Thr | Leu | Glu | Gln | Tyr | Ile | Tyr | Leu | |
| | | 1675 | | | | | 1680 | | | | | 1685 | | | | |
| TAC | AAC | TGT | CTG | AAC | AGC | GCA | CTG | CTG | AAC | GGG | CTG | CCC | AGA | GCT | GGG | 5319 |
| Tyr | Asn | Cys | Leu | Asn | Ser | Ala | Leu | Leu | Asn | Gly | Leu | Pro | Arg | Ala | Gly | |
| 1690 | | | | | 1695 | | | | | 1700 | | | | | 1705 | |
| AAG | TGG | CCT | GCG | CCC | TGC | TAGGCGTCAT | GTTCCAGCAA | ATCCACCCAG | | | | | | | | 5367 |
| Lys | Trp | Pro | Ala | Pro | Cys | | | | | | | | | | | |
| | | | | 1710 | | | | | | | | | | | | |

| | |
|---|---|
| GCCTGACTTC CCTAGGAGAG TGGATCCACC GGGCCTCACA CTGTCCAAGG GCAGAGTCCA | 5427 |
| GGAATAAAGA GACATGGTCA AAAAAAA | 5455 |

( 2 ) INFORMATION FOR SEQ ID NO:2:

( i ) SEQUENCE CHARACTERISTICS:
        ( A ) LENGTH: 1711 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Arg | Pro | Leu | Ile | Leu | Leu | Ala | Ala | Leu | Leu | Trp | Leu | Gln | Gly | Phe |
| 1 | | | | 5 | | | | | 10 | | | | | 15 | |
| Leu | Ala | Glu | Asp | Asp | Ala | Cys | Ser | Ser | Leu | Glu | Gly | Ser | Pro | Asp | Arg |

-continued

|     |     |     |     | 20  |     |     |     |     | 25  |     |     |     |     | 30  |
|-----|-----|-----|-----|-----|-----|-----|-----|-----|-----|-----|-----|-----|-----|-----|

Gln Gly Gly Gly Pro Leu Leu Ser Val Asn Val Ser Ser His Gly Lys
            35                      40                      45

Ser Thr Ser Leu Phe Leu Ser Trp Val Ala Ala Glu Leu Gly Gly Phe
        50                      55                      60

Asp Tyr Ala Leu Ser Leu Arg Ser Val Asn Ser Ser Gly Ser Pro Glu
65                      70                      75                      80

Gly Gln Gln Leu Gln Ala His Thr Asn Glu Ser Gly Phe Glu Phe His
                85                      90                      95

Gly Leu Val Pro Gly Ser Arg Tyr Gln Leu Lys Leu Thr Val Leu Arg
            100                     105                     110

Pro Cys Trp Gln Asn Val Thr Ile Thr Leu Thr Ala Arg Thr Ala Pro
            115                     120                     125

Thr Val Val Arg Gly Leu Gln Leu His Ser Ala Gly Ser Pro Ala Arg
        130                     135                     140

Leu Glu Ala Ser Trp Ser Asp Ala Pro Gly Asp Gln Asp Ser Tyr Gln
145                     150                     155                     160

Leu Leu Leu Tyr His Leu Glu Ser Gln Thr Leu Ala Cys Asn Val Ser
                165                     170                     175

Val Ser Pro Asp Thr Leu Ser Tyr Ser Phe Gly Asp Leu Leu Pro Gly
            180                     185                     190

Thr Gln Tyr Val Leu Glu Val Ile Thr Trp Ala Gly Ser Leu His Ala
        195                     200                     205

Lys Thr Ser Ile Leu Gln Trp Thr Glu Pro Val Pro Pro Asp His Leu
210                     215                     220

Ala Leu Arg Ala Leu Gly Thr Ser Ser Leu Gln Ala Phe Trp Asn Ser
225                     230                     235                     240

Ser Glu Gly Ala Thr Ser Phe His Leu Met Leu Thr Asp Leu Leu Gly
            245                     250                     255

Gly Thr Asn Thr Thr Ala Val Ile Arg Gln Gly Val Ser Thr His Thr
        260                     265                     270

Phe Leu His Leu Ser Pro Gly Thr Pro His Glu Leu Lys Ile Cys Ala
            275                     280                     285

Ser Ala Gly Pro His Gln Ile Trp Gly Pro Ser Ala Thr Glu Trp Thr
290                     295                     300

Tyr Pro Ser Tyr Pro Ser Asp Leu Val Leu Thr Pro Leu Arg Asn Glu
305                     310                     315                     320

Leu Trp Ala Ser Trp Lys Ala Gly Leu Gly Ala Arg Asp Gly Tyr Val
            325                     330                     335

Leu Lys Leu Ser Gly Pro Met Glu Ser Thr Ser Thr Leu Gly Pro Glu
        340                     345                     350

Glu Cys Asn Ala Val Phe Pro Gly Pro Leu Pro Pro Gly His Tyr Thr
            355                     360                     365

Leu Gln Leu Lys Val Leu Ala Gly Pro Tyr Asp Ala Trp Val Glu Gly
    370                     375                     380

Ser Thr Trp Leu Ala Glu Ser Ala Ala Leu Pro Arg Glu Val Pro Gly
385                     390                     395                     400

Ala Arg Leu Trp Leu Asp Gly Leu Glu Ala Ser Lys Gln Pro Gly Arg
            405                     410                     415

Arg Ala Leu Leu Tyr Ser Asp Asp Ala Pro Gly Ser Leu Gly Asn Ile
            420                     425                     430

Ser Val Pro Ser Gly Ala Thr His Val Ile Phe Cys Gly Leu Val Pro
        435                     440                     445

-continued

| | | | | | | | | | | | | | |
|---|---|---|---|---|---|---|---|---|---|---|---|---|---|
| Gly | Ala | His | Tyr | Arg | Val | Asp | Ile | Ala | Ser | Ser | Thr | Gly | Asp | Ile | Ser |
| | 450 | | | | 455 | | | | 460 | | | | |
| Gln | Ser | Ile | Ser | Gly | Tyr | Thr | Ser | Pro | Leu | Pro | Pro | Gln | Ser | Leu | Glu |
| 465 | | | | | 470 | | | | 475 | | | | | 480 |
| Val | Ile | Ser | Arg | Ser | Pro | Ser | Asp | Leu | Thr | Ile | Ala | Trp | Gly | Pro |
| | | | | 485 | | | | | 490 | | | | 495 | |
| Ala | Pro | Gly | Gln | Leu | Glu | Gly | Tyr | Lys | Val | Thr | Trp | His | Gln | Asp | Gly |
| | | | 500 | | | | | 505 | | | | | 510 | | |
| Ser | Gln | Arg | Ser | Pro | Gly | Asp | Leu | Val | Asp | Leu | Gly | Pro | Asp | Thr | Leu |
| | | 515 | | | | 520 | | | | | 525 | | | | |
| Ser | Leu | Thr | Leu | Lys | Ser | Leu | Val | Pro | Gly | Ser | Cys | Tyr | Thr | Val | Ser |
| | 530 | | | | 535 | | | | | 540 | | | | |
| Ala | Trp | Ala | Trp | Ala | Gly | Asn | Leu | Ser | Ser | Asp | Ser | Gln | Lys | Ile | His |
| 545 | | | | | 550 | | | | 555 | | | | | 560 |
| Ser | Cys | Thr | Arg | Pro | Ala | Pro | Thr | Asn | Leu | Ser | Leu | Gly | Phe | Ala |
| | | | | 565 | | | | 570 | | | | | 575 | |
| His | Gln | Pro | Ala | Ala | Leu | Lys | Ala | Ser | Trp | Tyr | His | Pro | Pro | Gly | Gly |
| | | | 580 | | | | | 585 | | | | | 590 | | |
| Arg | Asp | Ala | Phe | His | Leu | Arg | Tyr | Arg | Leu | Arg | Pro | Leu | Thr | Leu |
| | | | 595 | | | | 600 | | | | 605 | | | |
| Glu | Ser | Glu | Lys | Val | Leu | Pro | Arg | Glu | Ala | Gln | Asn | Phe | Ser | Trp | Ala |
| | 610 | | | | | 615 | | | | | 620 | | | | |
| Gln | Leu | Thr | Ala | Gly | Cys | Glu | Phe | Gln | Val | Gln | Leu | Ser | Thr | Leu | Trp |
| 625 | | | | | 630 | | | | | 635 | | | | | 640 |
| Gly | Ser | Glu | Arg | Ser | Ser | Ala | Asn | Ala | Thr | Gly | Trp | Thr | Pro | Pro |
| | | | | 645 | | | | 650 | | | | | 655 | |
| Ser | Ala | Pro | Thr | Leu | Val | Asn | Val | Thr | Ser | Asp | Ala | Pro | Thr | Gln | Leu |
| | | | 660 | | | | | 665 | | | | | 670 | | |
| Gln | Val | Ser | Trp | Ala | His | Val | Pro | Gly | Gly | Arg | Ser | Arg | Tyr | Gln | Val |
| | | 675 | | | | | 680 | | | | | 685 | | | |
| Thr | Leu | Tyr | Gln | Glu | Ser | Thr | Arg | Thr | Ala | Thr | Ser | Ile | Met | Gly | Pro |
| | 690 | | | | | 695 | | | | | 700 | | | | |
| Lys | Glu | Asp | Gly | Thr | Ser | Phe | Leu | Gly | Leu | Thr | Pro | Gly | Thr | Lys | Tyr |
| 705 | | | | | 710 | | | | | 715 | | | | | 720 |
| Lys | Val | Glu | Val | Ile | Ser | Trp | Ala | Gly | Pro | Leu | Tyr | Thr | Ala | Ala | Ala |
| | | | | 725 | | | | | 730 | | | | | 735 |
| Asn | Val | Ser | Ala | Trp | Thr | Tyr | Pro | Leu | Ile | Pro | Asn | Glu | Leu | Leu | Val |
| | | | 740 | | | | | 745 | | | | | 750 | | |
| Ser | Met | Gln | Ala | Gly | Ser | Ala | Val | Val | Asn | Leu | Ala | Trp | Pro | Ser | Gly |
| | | 755 | | | | | 760 | | | | | 765 | | | |
| Pro | Leu | Gly | Gln | Gly | Ala | Cys | His | Ala | Gln | Leu | Ser | Asp | Ala | Gly | His |
| | | 770 | | | | | 775 | | | | | 780 | | | |
| Leu | Ser | Trp | Glu | Gln | Pro | Leu | Lys | Leu | Gly | Gln | Glu | Leu | Phe | Met | Leu |
| 785 | | | | | 790 | | | | | 795 | | | | | 800 |
| Arg | Asp | Leu | Thr | Pro | Gly | His | Thr | Ile | Ser | Met | Ser | Val | Arg | Cys | Arg |
| | | | | 805 | | | | | 810 | | | | | 815 |
| Ala | Gly | Pro | Leu | Gln | Ala | Ser | Thr | His | Leu | Val | Val | Leu | Ser | Val | Glu |
| | | | 820 | | | | | 825 | | | | | 830 | | |
| Pro | Gly | Pro | Val | Glu | Asp | Val | Leu | Cys | His | Pro | Glu | Ala | Thr | Tyr | Leu |
| | | | 835 | | | | | 840 | | | | | 845 | | |
| Ala | Leu | Asn | Trp | Thr | Met | Pro | Ala | Gly | Asp | Val | Asp | Val | Cys | Leu | Val |
| | | 850 | | | | | 855 | | | | | 860 | | | |
| Val | Val | Glu | Arg | Leu | Val | Pro | Gly | Gly | Gly | Thr | His | Phe | Val | Phe | Gln |
| 865 | | | | | 870 | | | | | 875 | | | | | 880 |

```
Val Asn Thr Ser Gly Asp Ala Leu Leu Leu Pro Asn Leu Met Pro Thr
                885                 890                 895

Thr Ser Tyr Arg Leu Ser Leu Thr Val Leu Gly Arg Asn Ser Arg Trp
                900                 905                 910

Ser Arg Ala Val Ser Leu Val Cys Ser Thr Ser Ala Glu Ala Trp His
                915                 920                 925

Pro Pro Glu Leu Ala Glu Pro Pro Gln Val Glu Leu Gly Thr Gly Met
930                 935                 940

Gly Val Thr Val Met Arg Gly Met Phe Gly Lys Asp Asp Gly Gln Ile
945                 950                 955                 960

Gln Trp Tyr Gly Ile Ile Ala Thr Ile Asn Met Thr Leu Ala Gln Pro
                965                 970                 975

Ser Arg Glu Ala Ile Asn Tyr Thr Trp Tyr Asp His Tyr Tyr Arg Gly
                980                 985                 990

Cys Glu Ser Phe Leu Ala Leu Leu Phe Pro Asn Pro Phe Tyr Pro Glu
                995                 1000                1005

Pro Trp Ala Gly Pro Arg Ser Trp Thr Val Pro Val Gly Thr Glu Asp
1010                1015                1020

Cys Asp Asn Thr Gln Glu Ile Cys Asn Gly Arg Leu Lys Ser Gly Phe
1025                1030                1035                1040

Gln Tyr Arg Phe Ser Val Val Ala Phe Ser Arg Leu Asn Thr Pro Glu
                1045                1050                1055

Thr Ile Leu Ala Phe Ser Ala Phe Ser Glu Pro Arg Ala Ser Ile Ser
                1060                1065                1070

Leu Ala Ile Ile Pro Leu Thr Val Met Leu Gly Ala Val Val Gly Ser
                1075                1080                1085

Ile Val Ile Val Cys Ala Val Leu Cys Leu Leu Arg Trp Arg Cys Leu
                1090                1095                1100

Lys Gly Pro Arg Ser Glu Lys Asp Gly Phe Ser Lys Glu Leu Met Pro
1105                1110                1115                1120

Tyr Asn Leu Trp Arg Thr His Arg Pro Ile Pro Ile His Ser Phe Arg
                1125                1130                1135

Gln Ser Tyr Glu Ala Lys Ser Ala His Ala His Gln Thr Phe Phe Gln
                1140                1145                1150

Glu Phe Glu Glu Leu Lys Glu Val Gly Lys Asp Gln Pro Arg Leu Glu
                1155                1160                1165

Ala Glu His Pro Asp Asn Ile Ile Lys Asn Arg Tyr Pro His Val Leu
                1170                1175                1180

Pro Tyr Asp His Ser Arg Val Arg Leu Thr Gln Leu Pro Gly Glu Pro
1185                1190                1195                1200

His Ser Asp Tyr Ile Asn Ala Asn Phe Ile Pro Gly Tyr Ser His Thr
                1205                1210                1215

Gln Glu Ile Ile Ala Thr Gln Gly Pro Leu Lys Lys Thr Leu Glu Asp
                1220                1225                1230

Phe Trp Arg Leu Val Trp Glu Gln Gln Val His Val Ile Ile Met Leu
                1235                1240                1245

Thr Val Gly Met Glu Asn Gly Arg Val Leu Cys Glu His Tyr Trp Pro
1250                1255                1260

Ala Asn Ser Thr Pro Val Thr His Gly His Ile Thr Ile His Leu Leu
1265                1270                1275                1280

Ala Glu Glu Pro Glu Asp Glu Trp Thr Arg Arg Glu Phe Gln Leu Gln
                1285                1290                1295

His Gly Thr Glu Gln Lys Gln Arg Arg Val Lys Gln Leu Gln Phe Thr
```

|  |  |  | 1300 |  |  |  |  |  | 1305 |  |  |  |  | 1310 |  |
|---|---|---|---|---|---|---|---|---|---|---|---|---|---|---|---|

Thr Trp Pro Asp His Ser Val Pro Glu Ala Pro Ser Ser Leu Leu Ala
                    1315                         1320                    1325

Phe Val Glu Leu Val Gln Glu Gln Val Gln Ala Thr Gln Gly Lys Gly
          1330                         1335                    1340

Pro Ile Leu Val His Cys Ser Ala Gly Val Gly Arg Thr Gly Thr Phe
1345                    1350                         1355                    1360

Val Ala Leu Leu Arg Leu Leu Arg Gln Leu Glu Glu Glu Lys Val Ala
                         1365                         1370                    1375

Asp Val Phe Asn Thr Val Tyr Ile Leu Arg Leu His Arg Pro Leu Met
               1380                         1385                    1390

Ile Gln Thr Leu Ser Gln Tyr Ile Phe Leu His Ser Cys Leu Leu Asn
          1395                         1400                    1405

Lys Ile Leu Glu Gly Pro Pro Asp Ser Ser Asp Ser Gly Pro Ile Ser
1410                         1415                         1420

Val Met Asp Phe Ala Gln Ala Cys Ala Lys Arg Ala Ala Asn Ala Asn
1425                    1430                         1435                         1440

Ala Gly Phe Leu Lys Glu Tyr Lys Leu Leu Lys Gln Ala Ile Lys Asp
                    1445                         1450                    1455

Gly Thr Gly Ser Leu Leu Pro Pro Asp Tyr Asn Gln Asn Ser Ile
                    1460                         1465                    1470

Val Ser Arg Arg His Ser Gln Glu Gln Phe Ala Leu Val Glu Glu Cys
          1475                         1480                    1485

Pro Glu Asp Ser Met Leu Glu Ala Ser Leu Phe Pro Gly Gly Pro Ser
     1490                         1495                    1500

Gly Cys Asp His Val Val Leu Thr Gly Ser Ala Gly Pro Lys Glu Leu
1505                         1510                         1515                    1520

Trp Glu Met Val Trp Glu His Asp Ala His Val Leu Val Ser Leu Gly
                         1525                         1530                    1535

Leu Pro Asp Thr Lys Glu Lys Pro Pro Asp Ile Trp Pro Val Glu Met
          1540                         1545                    1550

Gln Pro Ile Val Thr Asp Met Val Thr Val His Arg Val Ser Glu Ser
          1555                         1560                    1565

Asn Thr Thr Thr Gly Trp Pro Ser Thr Leu Phe Arg Val Ile His Gly
1570                         1575                         1580

Glu Ser Gly Lys Glu Arg Gln Val Gln Cys Leu Gln Phe Pro Cys Ser
1585                    1590                         1595                    1600

Glu Ser Gly Cys Glu Leu Pro Ala Asn Thr Leu Leu Thr Phe Leu Asp
                    1605                         1610                    1615

Ala Val Gly Gln Cys Cys Phe Arg Gly Lys Ser Lys Lys Pro Gly Thr
                    1620                         1625                    1630

Leu Leu Ser His Ser Ser Lys Asn Thr Asn Gln Leu Gly Thr Phe Leu
                    1635                         1640                    1645

Ala Met Glu Gln Leu Leu Gln Gln Ala Gly Thr Glu Arg Thr Val Asp
     1650                         1655                    1660

Val Phe Asn Val Ala Leu Lys Gln Ser Gln Ala Cys Gly Leu Met Thr
1665                    1670                         1675                    1680

Pro Thr Leu Glu Gln Tyr Ile Tyr Leu Tyr Asn Cys Leu Asn Ser Ala
                    1685                         1690                    1695

Leu Leu Asn Gly Leu Pro Arg Ala Gly Lys Trp Pro Ala Pro Cys
                    1700                         1705                    1710

( 2 ) INFORMATION FOR SEQ ID NO:3:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /note= "This position is (I/V)."

( i x ) FEATURE:
    ( A ) NAME/KEY: Modified-site
    ( B ) LOCATION: 10
    ( D ) OTHER INFORMATION: /note= "This position is (S/T)."

( x i ) SEQUENCE DESCRIPTION: SEQ ID NO:3:

```
Xaa His Cys Xaa Ala Gly Xaa Xaa Arg Xaa Gly
1               5                   10
```

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Val His Cys Ser Ala Gly Val Gly Arg Thr Gly
1               5                   10
```

( 2 ) INFORMATION FOR SEQ ID NO:5:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Ser His Ser Ser Lys Asn Thr Asn Gln Leu Gly
1               5                   10
```

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Asp Tyr Ile Asn Ala
1               5
```

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CAGTGGATCC HGAYTAYATH AAYGC        2 5

( 2 ) INFORMATION FOR SEQ ID NO:8:

( i ) SEQUENCE CHARACTERISTICS:

(A) LENGTH: 7 amino acids
(B) TYPE: amino acid
(C) STRANDEDNESS: single
(D) TOPOLOGY: linear (xi) SEQUENCE DESCRIPTION: SEQ ID NO:8:

Tyr Ile Ala Thr Gln Gly Pro
1               5

(2) INFORMATION FOR SEQ ID NO:9:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:9:

CAGTGGATCC TACATYGYHR CMCARGG         27

(2) INFORMATION FOR SEQ ID NO:10:

(i) SEQUENCE CHARACTERISTICS:
(A) LENGTH: 6 amino acids
(B) TYPE: amino acid
(C) STRANDEDNESS: single
(D) TOPOLOGY: linear (xi) SEQUENCE DESCRIPTION: SEQ ID NO:10:

Lys Cys Asp Gln Tyr Trp
1               5

(2) INFORMATION FOR SEQ ID NO:11:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:11:

CAGTGGATCC AARTGYSMNS ARTAYTGGCC         30

(2) INFORMATION FOR SEQ ID NO:12:

(i) SEQUENCE CHARACTERISTICS:
(A) LENGTH: 8 amino acids
(B) TYPE: amino acid
(C) STRANDEDNESS: single
(D) TOPOLOGY: linear (xi) SEQUENCE DESCRIPTION: SEQ ID NO:12:

His Cys Ser Ala Gly Val Gly Arg
1               5

(2) INFORMATION FOR SEQ ID NO:13:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:13:

CTAGTCTAGA CCNAWDCCNG CRCARTG         27